(12) United States Patent
Rosin-Arbesfeld et al.

(10) Patent No.: US 10,987,370 B2
(45) Date of Patent: Apr. 27, 2021

(54) METHODS OF INDUCING READ-THROUGH OF A NONSENSE MUTATION ASSOCIATED WITH ATAXIA TELANGIECTASIA, RETT SYNDROME OR SPINAL MUSCULAR ATROPHY BY ERYTHROMYCIN OR AZITHROMYCIN

(71) Applicant: Ramot at Tel-Aviv University, Ltd., Tel Aviv (IL)

(72) Inventors: Rina Rosin-Arbesfeld, Herzlia (IL); Michal Caspi, Beit-Yehoshua (IL); Dalia Megiddo, Nataf (IL)

(73) Assignee: RAMOT AT TEL-AVIV UNIVERSITY LTD., Tel Aviv (IL)

( * ) Notice: Subject to any disclaimer, the term of this patent is extended or adjusted under 35 U.S.C. 154(b) by 0 days.

(21) Appl. No.: 14/652,368

(22) PCT Filed: Dec. 24, 2013

(86) PCT No.: PCT/IL2013/051058
§ 371 (c)(1),
(2) Date: Jun. 15, 2015

(87) PCT Pub. No.: WO2014/102778
PCT Pub. Date: Jul. 3, 2014

(65) Prior Publication Data
US 2015/0328247 A1    Nov. 19, 2015

Related U.S. Application Data

(60) Provisional application No. 61/745,651, filed on Dec. 24, 2012, provisional application No. 61/762,900, filed on Feb. 10, 2013.

(51) Int. Cl.
| | |
|---|---|
| *A61K 31/7048* | (2006.01) |
| *A61K 31/7052* | (2006.01) |
| *A61P 25/28* | (2006.01) |
| *A61P 25/00* | (2006.01) |
| *A61P 25/14* | (2006.01) |
| *G01N 33/53* | (2006.01) |
| *G01N 33/567* | (2006.01) |
| *A61K 49/00* | (2006.01) |
| *A61P 21/00* | (2006.01) |
| *G01N 33/50* | (2006.01) |

(52) U.S. Cl.
CPC ...... *A61K 31/7048* (2013.01); *A61K 31/7052* (2013.01); *A61P 21/00* (2018.01); *A61P 25/00* (2018.01); *A61P 25/14* (2018.01); *A61P 25/28* (2018.01); *G01N 33/5008* (2013.01); *G01N 2500/10* (2013.01)

(58) Field of Classification Search
CPC .. A61K 2300/00; A61K 31/343; A61K 31/19; A61K 31/192; A61K 31/425; A61K 31/56; A61K 31/70; A61K 39/395; A61K 45/00; A61K 31/216; A61K 31/35; A61K 31/355; A61K 31/375; A61K 31/40; A61K 31/41; A61K 31/7048; A61K 35/30; C12Q 1/6883; C12Q 2600/106; C12Q 2600/112; G01N 2800/2878; G01N 2800/2814; G01N 2800/385; G01N 33/5023; G01N 33/5041; G01N 33/5044; G01N 33/5058; C07C 311/37; C07D 213/75; C07D 215/227; C07D 215/44; C07D 221/10; C07D 231/14; C07D 233/88; C07D 239/47; C07D 261/06; C07D 261/14; C07D 261/18; C07D 263/48; C07D 267/14; C07D 277/46; C07H 21/00; C12N 2501/065
See application file for complete search history.

(56) References Cited

U.S. PATENT DOCUMENTS

| | | | |
|---|---|---|---|
| 4,331,803 A | 5/1982 | Watanabe | |
| 4,474,768 A | 10/1984 | Bright | |
| 4,517,359 A | 5/1985 | Kobrehel | |
| 4,668,625 A | 5/1987 | Cambiaghi | |
| 5,602,106 A | 2/1997 | Ajito | |
| 6,777,543 B2 | 8/2004 | Wu | |
| 6,825,171 B2 | 11/2004 | Wu | |
| 7,838,563 B2* | 11/2010 | DeJovin | A61K 31/137 514/649 |
| 7,888,366 B2* | 2/2011 | Singh | C07D 239/95 514/266.4 |

(Continued)

FOREIGN PATENT DOCUMENTS

| | | |
|---|---|---|
| WO | 0144516 | 6/2001 |
| WO | 200250093 | 6/2002 |

(Continued)

OTHER PUBLICATIONS

The fact sheet of Usher syndrome from the NEI website: nei.nih.gov/health/ushers/ushers retrieved on Apr. 23, 2018.*
The fact sheet of Ataxia Telangiectasia from the NCI website: www.cancer.gov/about-cancer/causes-prevention/genetics/ataxia-fact-sheet retrieved on Apr. 23, 2018.*

(Continued)

*Primary Examiner* — Chang-Yu Wang
(74) *Attorney, Agent, or Firm* — Browdy and Neimark, PLLC

(57) ABSTRACT

Disclosed is treatment of genetic neurodegenerative or neurodevelopmental diseases that are caused by or associated with nonsense mutations or premature termination codons using macrolides. Further disclosed are methods for identifying agents that induce read-through of nonsense mutations and premature termination codons and uses thereof.

3 Claims, 10 Drawing Sheets
Specification includes a Sequence Listing.

(56) References Cited

U.S. PATENT DOCUMENTS

| | | | | |
|---|---|---|---|---|
| 7,985,755 | B2* | 7/2011 | Singh | C07D 239/95 514/266.4 |
| 7,994,357 | B2* | 8/2011 | Huang | A61K 31/16 549/469 |
| 8,008,344 | B2* | 8/2011 | Huang | C07D 311/32 514/456 |
| 8,110,681 | B2* | 2/2012 | Heemskerk | C07D 209/46 544/144 |
| 8,211,631 | B2* | 7/2012 | Svendsen | C12N 5/0619 435/325 |
| 8,257,941 | B2* | 9/2012 | Sakurada | C12N 5/0696 435/29 |
| 8,318,801 | B2* | 11/2012 | Huang | A61K 31/16 514/469 |
| 8,367,678 | B2* | 2/2013 | Chang | A61K 31/4965 514/255.01 |
| 8,937,050 | B2* | 1/2015 | Talalay | A61K 31/145 514/24 |
| 9,328,346 | B2* | 5/2016 | Lee | |
| 9,371,336 | B2* | 6/2016 | Lee | C07D 491/04 |
| 2003/0236265 | A1* | 12/2003 | Sayada | C07D 513/18 514/252.13 |
| 2005/0171026 | A1* | 8/2005 | Hagiwara | A61K 31/7052 514/23 |
| 2005/0288314 | A1* | 12/2005 | Singh | C07D 239/95 514/266.2 |
| 2006/0018921 | A1* | 1/2006 | Levenson | A61K 31/19 424/191.1 |
| 2006/0276393 | A1* | 12/2006 | Milburn | A61K 31/05 514/183 |
| 2007/0072815 | A1* | 3/2007 | Kmiec | C12N 15/102 514/44 R |
| 2009/0042900 | A1* | 2/2009 | Singh | C07D 239/95 514/252.17 |
| 2009/0076130 | A1* | 3/2009 | Huang | C07D 311/32 514/456 |
| 2009/0306098 | A1* | 12/2009 | Green | A61K 31/52 514/263.4 |
| 2009/0311695 | A1 | 12/2009 | Nasim | |
| 2009/0312323 | A1* | 12/2009 | Heemskerk | C07D 209/46 514/235.2 |
| 2009/0324559 | A1* | 12/2009 | Sakurada | C12N 5/0696 424/93.7 |
| 2010/0152204 | A1* | 6/2010 | Chang | A61K 31/4965 514/255.06 |
| 2010/0204149 | A1* | 8/2010 | Bevec | A61K 38/12 514/6.9 |
| 2010/0234402 | A1* | 9/2010 | Dreyfuss | A61K 31/015 514/263.33 |
| 2010/0240090 | A1* | 9/2010 | Sakurada | C12N 5/0696 435/29 |
| 2010/0256401 | A1* | 10/2010 | Huang | A61K 31/16 549/469 |
| 2010/0267712 | A1* | 10/2010 | Heemskerk | C07D 403/04 514/230.5 |
| 2010/0279893 | A1* | 11/2010 | Svendsen | C12N 5/0619 506/10 |
| 2010/0305167 | A1* | 12/2010 | Burk | A61K 31/4406 514/357 |
| 2011/0112118 | A1* | 5/2011 | Singh | C07D 239/95 514/266.4 |
| 2011/0224294 | A1* | 9/2011 | Huang | A61K 31/16 514/469 |
| 2011/0312897 | A1* | 12/2011 | Allis | A61K 38/05 514/19.3 |
| 2011/0319353 | A1* | 12/2011 | Chang | A61K 31/4965 514/34 |
| 2012/0077753 | A1* | 3/2012 | Gangwani | A61K 31/416 514/17.7 |
| 2012/0083495 | A1* | 4/2012 | Heemskerk | C07D 209/46 514/235.2 |
| 2012/0264648 | A1* | 10/2012 | Svendsen | C12N 5/0619 506/14 |
| 2012/0277158 | A1* | 11/2012 | Castaigne | A61P 25/18 514/17.5 |
| 2013/0123203 | A1* | 5/2013 | Talalay | A61K 31/145 514/24 |
| 2015/0005289 | A1* | 1/2015 | Qi | C07D 471/04 514/210.21 |
| 2015/0051288 | A1* | 2/2015 | Talalay | A61K 31/145 514/588 |
| 2015/0080383 | A1* | 3/2015 | Yang | C07D 311/30 514/218 |
| 2015/0119380 | A1* | 4/2015 | Woll | C07D 405/14 514/210.21 |
| 2015/0126515 | A1* | 5/2015 | Chen | C07D 405/14 514/249 |
| 2015/0166575 | A1* | 6/2015 | Lee | C07D 491/04 514/218 |
| 2015/0238483 | A1* | 8/2015 | Lefebvre | A61K 45/06 514/8.6 |

FOREIGN PATENT DOCUMENTS

| | | |
|---|---|---|
| WO | 02056892 | 7/2002 |
| WO | WO2004/001010 | 12/2003 |
| WO | WO2005/118610 | 12/2005 |
| WO | WO2007/022076 | 2/2007 |
| WO | WO2007022076 | * 2/2007 |
| WO | WO2007/027106 | 3/2007 |
| WO | 2007144876 | 12/2007 |
| WO | WO2007/144876 | 12/2007 |
| WO | WO2009/033660 | * 3/2009 |
| WO | WO2010/084201 | 7/2010 |
| WO | WO2012/016930 | 2/2012 |
| WO | 2014102778 | 7/2014 |

OTHER PUBLICATIONS

The fact sheet of Rett Syndrome from US National Library of Medicine website: ghr.nlm.nih.gov/condition/rett-syndrome retrieved on Apr. 23, 2018.*

Use of Azithromycin from the RxList website: www.rxlist.com/consumer_azithromycin_zithromax/drugs-condition.htm retrieved on Apr. 23, 2018.*

Systemic antibiotics recommendations from the American Academy of Dermatology association website: www.aad.org/practicecenter/quality/clinical-guidelines/acne/systemic-antibiotics retrieved on Apr. 23, 2018.*

Jaruratanasirikul et al. Antimicrobial Agents and Chemotherapy 1996; 40:825-826.*

Tissi et al. Antimicrobial Agents and Chemotherapy 1995; 39: 1938-1947.*

The factsheet of antibiotics related to Torsades De Pointes from CredibleMed, retrieved from the crediblemeds.org website on Dec. 11, 2018.*

Osman et al. J. Neuromuscular disease 2017, 4:237-249.*

Davies, Expert Rev. Clin. Immunol. 2009; 5:565-575.*

Weaving et al. J. Med. Genet. 2005; 42:1-7.*

Du et al. J. Exp. Med. 2009; 206: 2285-2297, published online Sep. 21, 2009.*

Gatti Ann N. Y. Acad. Sci. 2012; 1250:33-40.*

The factsheet of missense mutation from the Genetics Home Reference retrieved from the US Natuional Library of Medicine website: https://ghr.nlm.nih.gov/primer/mutationsanddisorders/possiblemutations on May 29, 2019.*

Na et al. J. Neurosci. 2012; 32(9): . doi:10.1523/JNEUROSC1.6000-11.2012.*

Certegni et al. Am. J. Hum. Genet. 2006; 78:63-77.*

Verhagen et al., Human Mutation; 2011, published online Dec. 28, 2011.*

Kozlov et al.,J. Biol. Chem. 2003; 278:9309-9317.*

Ray et al., N. Engl. J Med. 2012; 366:1881-90.*

Thistlethwaite et al., J. Mol. Diagn. 2003; 5:121-126.*

De Bona et al., Eur. J. Hum. Genet. 2000; 8:325-330.*

Lorson et al., Proc. Natl. Acad. Sci. USA, 1999; 96:6307-6311.*

(56) References Cited

OTHER PUBLICATIONS

Wolstencroft et al. Hum. Mol. Genet. 2005; 14:1199-1210.*
Coutinho dos Santos et al., Pediatr. Neurol. 2009; 40:117-119.*
Bidou and Allamand (Apr. 2018) Nonsense Mutations Causing Inherited Disease:Therapeutic Approaches. DOI:10.1002/9780470015902.a0022433.pub2.*
Lee and Dougherty, Pharmacol. Thera. 2012; 136:227-266.*
International Search Report from corresponding PCT International Application No. PCT/IL2013/051058, dated Jun. 23, 2014.
Auld et al., "Molecular basis for the high-affinity binding and stabilization of firefly luciferase by PTC124" *PNAS*, 2010, 107(11): 4878-4883.
Burke et al., "Suppression of a nonsense mutation in mammalian cells in vivo by the aminoglycoside antibiotics G-418 and paromomycin" *Nucleic Acids Research*, 1985,13(17): 6265-6272.
Butchbach et al., "Effects of 2,4-diaminoquinazoline derivatives on SMN expression and phenotype in a mouse model for spinal muscular atrophy" *Human Molecular Genetics*, 2010, vol. 19, No. 3, pp. 454-467.
Cardno et al., "A homogeneous cell-based bicistronic fluorescence assay for high-throughput identification of drugs that perturb viral gene recoding and read-through of nonsense stop codons" *RNA*, 2009, vol. 15, No. 8, pp. 1614-1621.
Du et al., "Nonaminoglycoside compounds induce readthrough of nonsense mutations" *J. Exp. Med.*, 2009, vol. 206, No. 10, pp. 2285-2297.
Floquet et al., Statistical Analysis of Readthrough Levels for Nonsense Mutations in Mammalian Cells Reveals a Major Determinant of Response to Gentamicin *PLoS Genetics*, 2012, vol. 8, Issue 3: e1002608.
Hainrichson et al., "Designer aminoglycosides: the race to develop improved antibiotics and compounds for the treatment of human genetic diseases" *Org. Biomol. Chem.*, 2008, 6(2): 227-239.
Hua et al., "Peripheral SMN restoration is essential for long-term rescue of a severe SMA mouse model" *Nature*, 2011, 478(7367):123-126.
Jaruratanasirikul et al., "Distribution of Azithromycin into Brain Tissue, Cerebrospinal Fluid, and Aqueous Humor of the Eye" *Antimicrobial Agents and Chemotherapy*, 1996, vol. 40, No. 3, pp. 825-826.
Lai et al., "Correction of ATM gene function by aminoglycoside-induced read-through of premature termination codons" *PNAS*, 2004, vol. 101, No. 44, pp. 15676-15681.
Lorson and Lorson "SMN-inducing compounds for the treatment of spinal muscular atrophy", *Future Med Chem.*, 2012, 4(16): 2067-2084.
Malik et al., "Aminoglycoside-induced mutation suppression (stop codon readthrough) as a therapeutic strategy for Duchenne muscular dystrophy" *Ther Adv Neurol Disord*, 2010, 3(6): 379-389.
Mattis et al., "Delivery of a read-through inducing compound, TC007, lessens the severity of a spinal muscular atrophy animal model" *Human Molecular Genetics*, 2009, vol. 18, No. 20: 3906-3913.
Mendell et al., "When the Message Goes Awry: Disease-Producing Mutations that Influence mRNA Content and Performance" *Cell*, 2001, vol. 107(4): 411-414.
Thompson et al., "Effects of a Number of Classes of 50S Inhibitors on Stop Codon Readthrough during Protein Synthesis" *Antimicrobial Agents and Chemotherapy*, 2004, vol. 48, No. 12, pp. 4889-4891.
Zilberberg et al., "Restoration of APC gene function in colorectal cancer cells by aminoglycoside- and macrolide-induced read-through of premature termination codons" *Gut*, 2010 59: 496-507.
Zingman et al., "Aminoglycoside-induced Translational Readthrough in Disease: Overcoming Nonsense Mutations by Pharmacogenetic Therapy" *Clinical Pharmacology & Therapeutics*, 2007, vol. 81, No. 1, pp. 99-103.
Barrett et al., (2005) Validated HPLC-MS-MS method for determination of azithromycin in human plasma. Analytical and bioanalytical chemistry, 383(2), 210-217.

El Mansari & Blier, (2008) In vivo electrophysiological assessment of the putative antidepressant Wf-516 in the rat raphe dorsalis, locus coeruleus and hippocampus. Naunyn-Schmiedeberg's archives of pharmacology, 376(5), 351-361.
Glascock et al., (2011) Delivery of therapeutic agents through intracerebroventricular (ICV) and intravenous (IV) injection in mice. JoVE (Journal of Visualized Experiments), pp. 1-4, (56), e2968-e2968.
Heier & DiDonato, (2009) Translational readthrough by the aminoglycoside geneticin (G418) modulates SMN stability in vitro and improves motor function in SMA mice in vivo. Human molecular genetics, 18(7), 1310-1322.
Le et al., (2005) SMNΔ7, the major product of the centromeric survival motor neuron (SMN2) gene, extends survival in mice with spinal muscular atrophy and associates with full-length SMN. Human molecular genetics, 14(6), 845-857.
Manuvakhova et al., (2000) Aminoglycoside antibiotics mediate context-dependent suppression of termination codons in a mammalian translation system. Rna, 6(7), 1044-1055.
Mattis et al., (2009) Subcutaneous administration of TC007 reduces disease severity in an animal model of SMA. BMC neuroscience, pp. 1-6, 10(1), 142.
Nau et al., (2010) Penetration of drugs through the blood-cerebrospinal fluid/blood-brain barrier for treatment of central nervous system infections. Clinical microbiology reviews, 23(4), 858-883.
Osborne et al., (2012) Characterization of behavioral and neuromuscular junction phenotypes in a novel allelic series of SMA mouse models. Human molecular genetics, pp. 4431-4447, vol. 21, No. 20.
Saijo et al., (2012) Presynaptic selectivity of a ligand for serotonin 1A receptors revealed by in vivo PET assays of rat brain. PloS one, pp. 1-13, 7(8), e42589.
Seo et al., (2013) Spinal muscular atrophy: an update on therapeutic progress. Biochimica Et Biophysica Acta (BBA)—Molecular Basis of Disease, 1832(12), 2180-2190.
Wolstencroft et al., (2005) A non-sequence-specific requirement for SMN protein activity: the role of aminoglycosides in inducing elevated SMN protein levels. Human molecular genetics, 14(9), 1199-1210.
Condition, gene or chromosome summary: National Library of Medicine (US). Genetics Home Reference [Internet]. Bethesda (MD): The Library; Ataxia-telangiectasia; [reviewed Jan. 2013; cited Jan. 16, 2018]. Available from: https://ghr.nlm.nih.gov/condition/ataxia-telangiectasia.
Condition, gene or chromosome summary: National Library of Medicine (US). Genetics Home Reference [Internet]. Bethesda (MD): The Library; Rett-syndrome [reviewed Dec. 2013; cited Jan. 16, 2018]. Available from: https://ghr.nlm.nih.gov/condition/rett-syndrome.
Condition, gene or chromosome summary: National Library of Medicine (US). Genetics Home Reference [Internet]. Bethesda (MD): The Library; Spinal-muscular-atrophy [reviewed Jan. 2013; cited Jan. 16, 2018]. Available from: https://ghr.nlm.nih.gov/condition/spinal-muscular-atrophy.
Condition, gene or chromosome summary: National Library of Medicine (US). Genetics Home Reference [Internet]. Bethesda (MD): The Library; Usher-syndrome [reviewed Nov. 2017; cited Jan. 16, 2018]. Available from: https://ghr.nlm.nih.gov/condition/usher-syndrome.
Part:BBa_K1732014; Designed by: Donna Lee, Group: iGEM15_Carnegie_Mellon, Sep. 9, 2015 (Sep. 9, 2015). Retrieved from: http://parts.igem.org/Part:BBa_K1732014 on Jul. 1, 2020. 3 pages.
Caspi et al., (2016) A flow cytometry-based reporter assay identities macrolide antibiotics as nonsense mutation read-through agents. J Mol Med (Berl) 94(4): 469-82.
Crivat and Taraska (2012) Imaging proteins inside cells with fluorescent tags. Trends Biotechnol 30(1): 8-16.
Grentzmann et al., (1998) A dual-luciferase reporter system for studying recoding signals. RNA 4(4): 479-86.
Halvey et al., (2012) A Reporter System for Translational Readthrough of Stop Codons in Human Cells. FEBS Open Bio 2: 56-59.

(56) References Cited

OTHER PUBLICATIONS

Pérez et al., (2012) Readthrough strategies for therapeutic suppression of nonsense mutations in inherited metabolic disease. Mol Syndromol 3(5): 230-6.

Rosin-Arbesfeld et al., (2015) 292 Macrolide Induced Read-Through of APC Nonsense Mutations in Familial Adenomatous Polyposis. Gastroenterology 148(4): S-63.

* cited by examiner

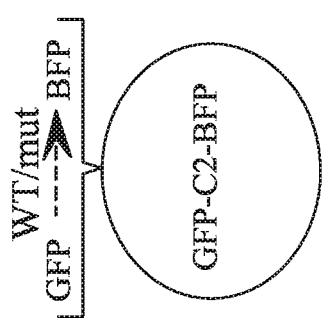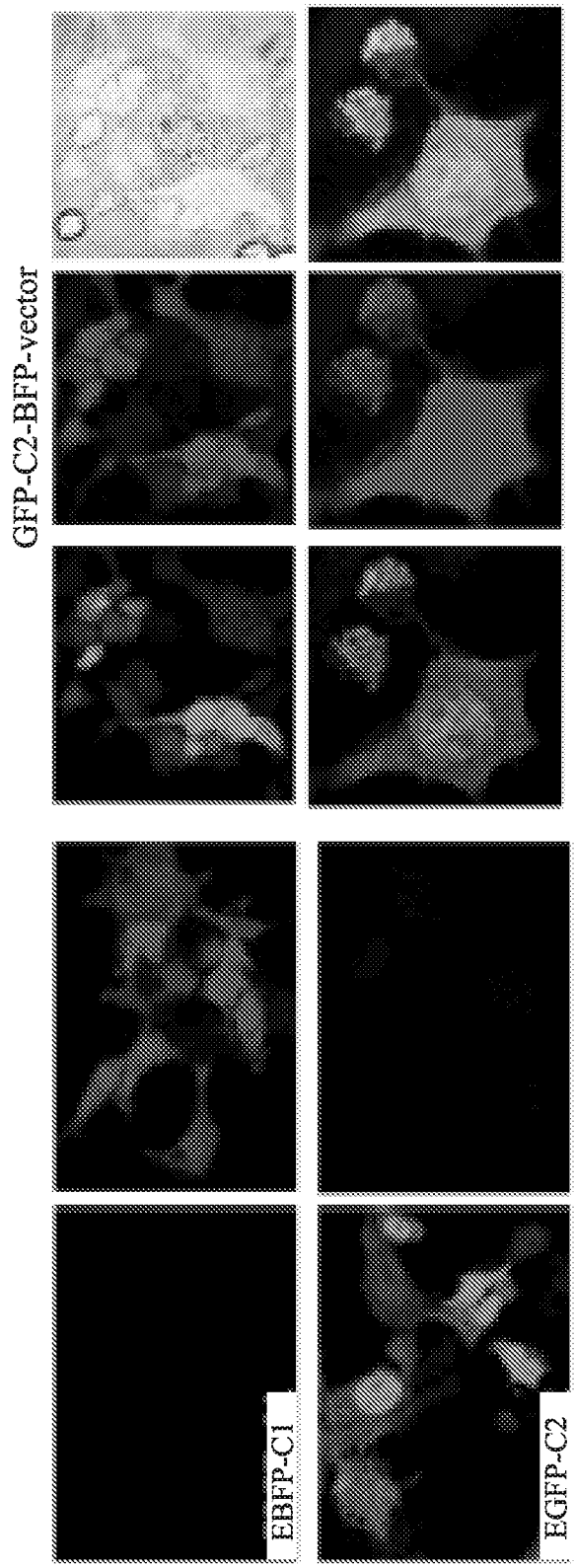
Fig. 1A
Fig. 1B

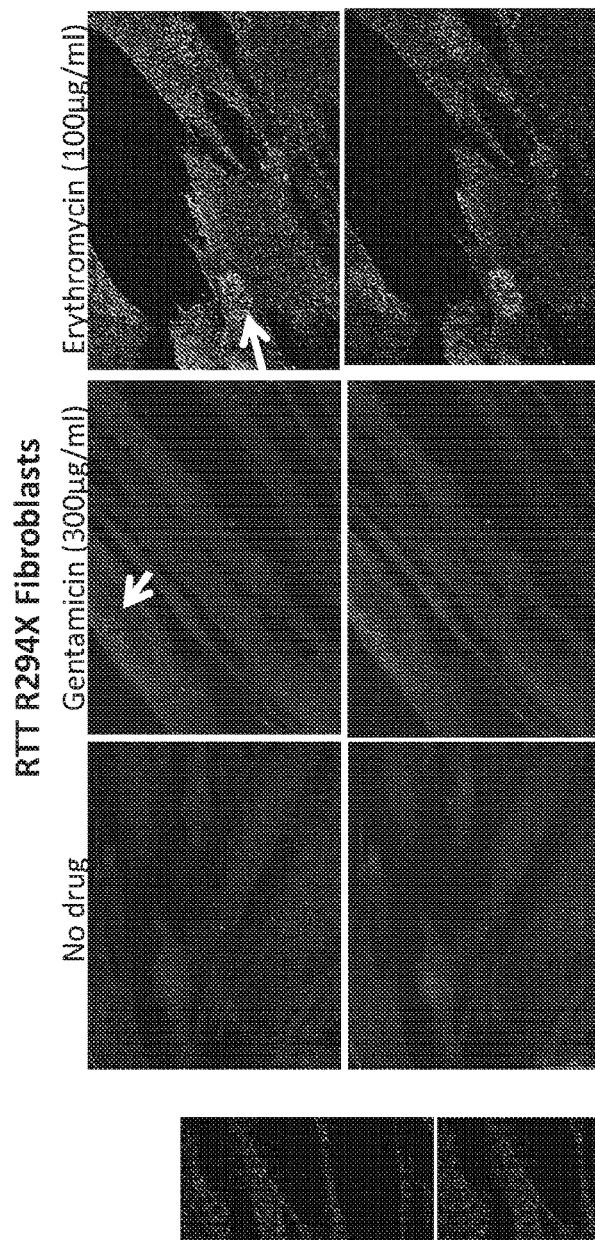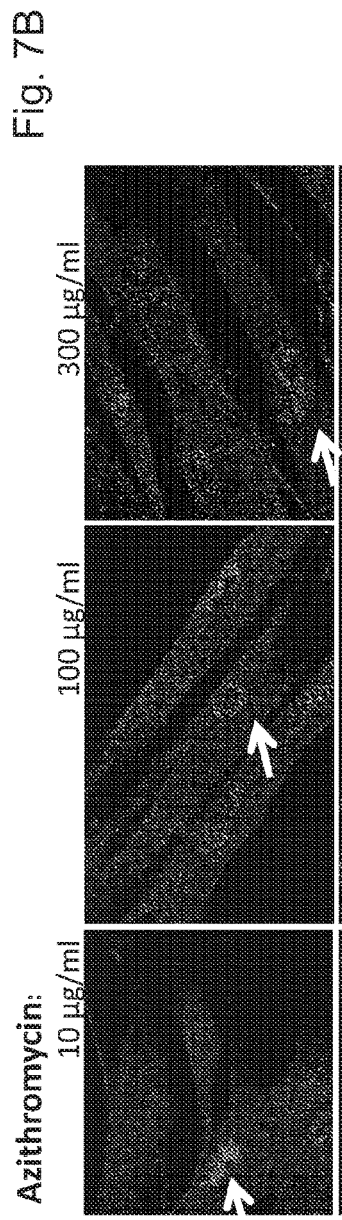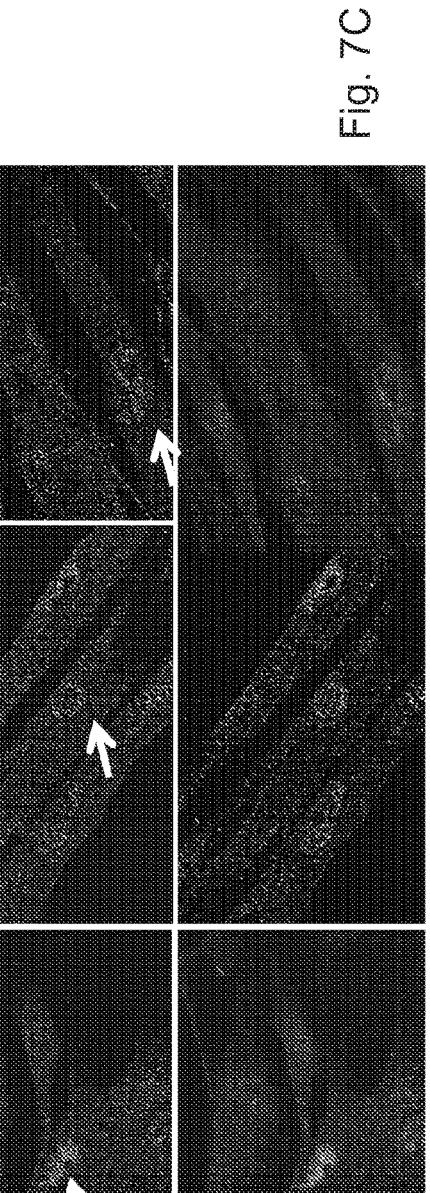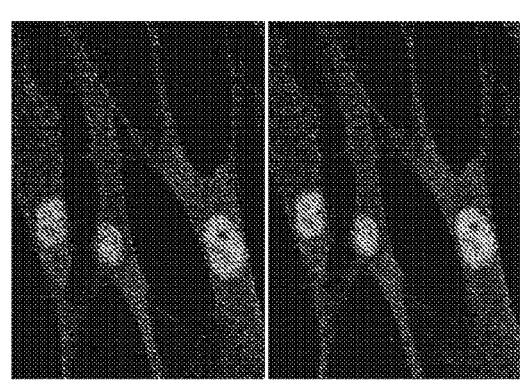

METHODS OF INDUCING READ-THROUGH OF A NONSENSE MUTATION ASSOCIATED WITH ATAXIA TELANGIECTASIA, RETT SYNDROME OR SPINAL MUSCULAR ATROPHY BY ERYTHROMYCIN OR AZITHROMYCIN

CROSS-REFERENCE TO RELATED APPLICATIONS

This application is the U.S. National Stage of International Patent Application No. PCT/IL2013/051058, filed Dec. 24, 2013, which claims priority to and benefit of U.S. Provisional Application No. 61/745,651, filed on Dec. 12, 2012, and U.S. Provisional Application No. 61/762,900, filed on Feb. 10, 2013.

FIELD OF THE INVENTION

The present disclosure relates to treatment of genetic neurodegenerative or neurodevelopmental diseases that are caused by nonsense mutations using macrolides. The present invention further relates to methods for identifying agents that induce read-through of nonsense mutations.

SEQUENCE LISTING

The present application contains a Sequence Listing which has been submitted in ASCII format via EFS-Web and is hereby incorporated by reference in its entirety. Said ASCII copy, created on Dec. 23, 2013, is named 2248743_ST25.txt and is 5,839 bytes in size.

BACKGROUND OF THE INVENTION

The advent of modern human genetics has revealed that many rare, orphan diseases are genetic in origin (1). Particularly, diseases such as Rett syndrome, Duchenne muscular dystrophy, Usher syndrome and many other diseases have been shown to result in most cases from nonsense mutations, which are single-nucleotide variations within the coding sequence of a gene that result in a premature termination codon. The presence of such mutations leads to the synthesis of a truncated non-functional protein.

Over the past ten years, treatment strategies of genetic diseases resulting from nonsense mutations within the coding sequence of a gene have emerged based on the use of aminoglycoside antibiotics. These molecules facilitate the read-through of premature termination codons, thus restoring the synthesis of a full-length protein. Such strategies have been tested for various genetic diseases, including Duchenne muscular dystrophy and cystic fibrosis (2-6). Unfortunately, aminoglycosides, such as gentamicin, have serious dose-limiting toxicities, rendering them an unattractive long term treatment for any chronic disorder (7).

The read-through level of a certain mutated gene by a certain molecule depends on the nature of the stop codon and the surrounding nucleotide context (8). Thus, the response to a certain treatment using a read-through agent is highly variable and little is known about the rules governing the read-through level, namely, the level of synthesis of a full length protein.

The effect of a number of antibiotic agents on stop codon read-through during protein synthesis in a prokaryotic system (*Escherichia coli*) has been examined (9). In addition, the restoration of adenomatous polyposis coli (APC) gene function in colorectal cancer cells by aminoglycoside- and macrolide-induced read-through of premature termination codons has also been reported by Zilberberg et al. as well as in the patent application WO 2007/144876 (10, 11). In particular, WO 2007/144876 discloses the use of a macrolide antibiotic for the manufacture of a medicament for the treatment or prevention of various cancers and specifically cancers that express a mutated APC gene.

Traditionally, vectors designed for testing read-through of premature termination codons were based on luciferase. However, such assays were found to have off-target effects, suggesting that the leading compounds identified by these assays may not actually induce read-through (12). Various approaches for screening assays for identifying readthrough agents are described, for example, in Du et al., and Cardno et al. (13, 14).

In particular, the patent application WO 2004/001010 (15) discloses methods for screening and identifying compounds that modulate premature translation termination and/or nonsense-mediated messenger ribonucleic acid ("mRNA") decay by screening and identifying compounds that modulate the post-transcriptional expression of any gene with a premature translation stop codon. The patent application WO 2007/027106 (16) discloses dual-reporter recoding constructs and methods. Such constructs and methods are useful for screening for drugs that act via modulating recoding.

In addition, the patent application US 2009/0311695 (17) discloses methods for determining the effect of a genetic variation on the integrity of an RNA transcript and/or on RNA metabolism. US 2009/0311695 also discloses high throughput assays for identifying agents that modulate the integrity of the RNA transcript and/or are involved in modulating RNA metabolism.

There is still a need for therapeutic agents useful for treating genetic diseases, in particular genetic diseases caused by nonsense mutations or premature stop codons, primarily since the current potential treatment suffers from disadvantages such as toxicity and relatively low levels of synthesis of the full length protein. To date, no proposed read-through treatment has yet been found effective in clinical studies. In addition, there is a further need for efficient, yet simple, compositions and methods for identifying nonsense mutation read-through agents, which may be used as therapeutic agents for genetic diseases caused by nonsense mutations.

SUMMARY OF THE INVENTION

In one of its aspects the present disclosure provides a composition comprising at least one antibiotic macrolide for use in a method of treating a genetic neurodegenerative or neurodevelopmental disease associated with a premature stop codon or with a nonsense mutation in a patient in need thereof.

In another one of its aspects the present disclosure provides a composition comprising at least one antibiotic macrolide for use in a method of treating a genetic neurodegenerative or neurodevelopmental disease associated with a nonsense mutation in a patient in need thereof, wherein said composition is administered non-systemically.

In yet another one of its aspects the present disclosure provides a composition comprising at least one antibiotic macrolide for use in a method of treating a genetic neurodegenerative or neurodevelopmental disease associated with a nonsense mutation in a patient in need thereof, wherein said composition is administered non-systemically and wherein said at least one antibiotic macrolide induces read-through of said nonsense mutation.

In some embodiments the at least one antibiotic macrolide according to the present disclosure is identified by the method comprising:

a. contacting a candidate antibiotic macrolide with a population of cells containing a nucleic acid construct comprising: (i) an upstream nucleic acid sequence encoding a fluorescent protein selected from GFP and BFP; (ii) a downstream nucleic acid sequence encoding a fluorescent protein different from the upstream fluorescent protein and selected from GFP and BFP; and (iii) a nucleic acid sequence comprising a nonsense mutation associated with said genetic neurodegenerative or neurodevelopmental disease, interposed between the upstream and downstream nucleic acid sequences; wherein the upstream, downstream and interposed nucleic acid sequences are linked in-frame in a single ORF; and b. measuring the fluorescence of the downstream fluorescent protein;

wherein an increase in the fluorescence level of the downstream fluorescent protein in the cells containing said nucleic acid construct contacted with said candidate antibiotic macrolide compared to cells containing said nucleic acid construct and not contacted with said candidate antibiotic macrolide is indicative that the candidate antibiotic macrolide induces read-through of said nonsense mutation.

In other embodiments the composition according to the present disclosure is directly administered to the CNS in a therapeutically effective dose.

In still another one of its aspects the present disclosure provides a composition comprising at least one antibiotic macrolide for use in at least partially restoring production of an intra-cellular or subcellular functional protein, thereby treating at least one symptom or condition of a genetic neurodegenerative or neurodevelopmental disease associated with production of said intra-cellular or subcellular protein in a non-functional form resulting from at least one nonsense mutation.

In some embodiments the composition according to the present disclosure is wherein said at least partially restoring production of said intra-cellular functional protein is at least 7% production of functional protein, of total protein produced.

In other embodiments the composition according to the present disclosure is wherein said at least partially restoring production of said intra-cellular functional protein is between about 7% to about 25% production of functional protein, of total protein produced.

In further embodiments the at least one macrolide according to the present disclosure is selected from a group consisting of erythromycin, azithromycin and clarithromycin or any combination of at least two thereof.

In still further embodiments the composition according to the present disclosure is administered in a route of administration selected from the group consisting of intrathecal, intraneural, intra-cerebral, intra-ventricular and intra-cranial.

In some embodiments the composition according to the present disclosure is administered intrathecally.

In other embodiments the genetic neurodegenerative or neurodevelopmental disease according to the present disclosure is selected from the group consisting of Spinal Muscular Atrophy, Ataxia-telangiectasia, Rett syndrome, Usher syndrome, a peroxisome biogenesis disorder, Activator Deficiency/GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease, GM1 gangliosidosis, I-Cell disease/Mucolipidosis II, Infantile Free Sialic Acid Storage Disease/ISSD, Juvenile Hexosaminidase A Deficiency, Krabbe disease, Lysosomal acid lipase deficiency, Metachromatic Leukodystrophy, Mucopolysaccharidoses disorders, Multiple sulfatase deficiency, Niemann-Pick Disease, Neuronal Ceroid Lipofuscinoses, Pompe disease/Glycogen storage disease type II, Pycnodysostosis, Sandhoff disease/Adult Onset/GM2 Gangliosidosis, Sandhoff disease/GM2 gangliosidosis—Infantile, Sandhoff disease/GM2 gangliosidosis—Juvenile, Schindler disease, Salla disease/Sialic Acid Storage Disease, Tay-Sachs/GM2 gangliosidosis, Wolman disease, Spinocerebellar ataxia, Autosomal recessive spastic ataxia of Charlevoix-Saguenay, Episodic ataxias (Eas), autosomal recessive cerebellar ataxias (ARCAs), Parkinson's disease, Taupaties, Progroid syndrome, Werner syndrome, Polyneuropathy, hearing loss, ataxia, retinitis pigmentosa, and cataract (PHARC), Charcot-Marie-Tooth (CMT), Prion diseases, infantile neuronal ceroid lipofuscinosis, familial encephalopathy with neuroserpin inclusion bodies, Darier's disease, Laminopathies, Emery-Dreifuss muscular dystrophy, limb girdle muscular dystrophy type 1B, Dunnigan-type familial partial lipodystrophy, Barraquer-Simons syndrome, Buschke-Ollendorff syndrome, Familial partial lipodystrophy of the Dunnigan type (FPLD), Leukodystrophy, demyelinating, adult-onset, autosomal dominant (ADLD), Pelizaeus-Merzbacher disease, and any combinations thereof.

In still another one of its aspects the present disclosure provides a composition comprising at least one antibiotic macrolide for use in a method of treating Spinal Mascular Atrophy (SMA) in a patient in need thereof.

In some embodiments the at least one antibiotic macrolide according to the present disclosure increases the production of full length SMN2.

In some embodiments the composition according to the present disclosure is administered non-systemically.

In other embodiments the at least one antibiotic macrolide according to the present disclosure induces read-through of a premature stop codon present in the SMN2 gene.

In further embodiments the at least one antibiotic macrolide according to the present disclosure is identified by the method comprising:

a. contacting a candidate antibiotic macrolide with a population of cells containing a nucleic acid construct comprising: (i) an upstream nucleic acid sequence encoding a fluorescent protein selected from GFP and BFP; (ii) a downstream nucleic acid sequence encoding a fluorescent protein different from the upstream fluorescent protein and selected from GFP and BFP; and (iii) a nucleic acid sequence of at least 45 nucleotides corresponding to a fragment of the SMN2 gene comprising a stop codon present in said SMN2 gene, interposed between the upstream and downstream nucleic acid sequences; wherein the upstream, downstream and interposed nucleic acid sequences are linked in-frame in a single ORF; and b. measuring the fluorescence of the downstream fluorescent protein;

wherein an increase in the fluorescence level of the downstream fluorescent protein in the cells containing said nucleic acid construct contacted with said candidate antibiotic macrolide compared to cells containing said nucleic acid construct and not contacted with said candidate antibiotic macrolide is indicative that the candidate antibiotic macrolide induces read-through of said stop codon.

In still further embodiments the composition according to the present disclosure is administered directly to the CNS.

In another one of its aspects the present disclosure provides a method of treating a genetic neurodegenerative or neurodevelopmental disease associated with a nonsense mutation in a patient in need thereof, said method comprising administering a composition comprising at least one antibiotic macrolide.

In still another one of its aspects the present disclosure provides a method of treating a genetic neurodegenerative or neurodevelopmental disease associated with a nonsense mutation in a patient in need thereof, said method comprising administering a composition comprising at least one antibiotic macrolide, wherein said composition is administered non-systemically.

The present disclosure further provides a method of treating a genetic neurodegenerative or neurodevelopmental disease associated with a nonsense mutation in a patient in need thereof, said method comprising administering a composition comprising at least one antibiotic macrolide, wherein said composition is administered non-systemically and wherein said at least one antibiotic macrolide induces read-through of said nonsense mutation.

In another one of its aspects the present disclosure provides a method of restoring at least partial production of an intra-cellular or subcellular functional protein, said method comprising administering a composition comprising at least one antibiotic macrolide, thereby treating at least one symptom or condition of a genetic neurodegenerative or neurodevelopmental disease associated with production of said intra-cellular or subcellular protein in a non-functional form resulting from at least one nonsense mutation.

In some embodiments the method according to the present disclosure is wherein said restoring at least partial production of said intra-cellular functional protein is at least 7% production of functional protein, of total protein produced.

In other embodiments the method according to the present disclosure is wherein said restoring at least partial production of said intra-cellular functional protein is between about 7% to about 25% production of functional protein, of total protein produced.

In another one of its aspects the present disclosure provides a method of treating Spinal Mascular Atrophy (SMA) in a patient in need thereof, said method comprising administering a composition comprising at least one antibiotic macrolide.

In still another one of its aspects the present disclosure provides a nucleic acid construct comprising:
  a. a first nucleic acid sequence encoding a green-fluorescence-protein (GFP);
  b. a second nucleic acid sequence encoding a blue-fluorescence-protein (BFP); and
  c. a third nucleic acid sequence of at least 45 nucleotides interposed between the first and second nucleic acid sequences, wherein the third nucleic acid sequence comprises a nonsense mutation;
  wherein the first, second and third nucleic acid sequences are linked in-frame in a single open reading frame (ORF).

In some embodiments the nucleic acid construct according to the present disclosure is wherein GFP is upstream to BFP.

In other embodiments the nucleic acid construct according to the present disclosure further comprises one or more linker nucleic acid sequences interposed between the first, second and third nucleic acid sequences.

The present disclosure further provides a vector comprising the nucleic acid construct as herein defined.

In another one of its aspects the present disclosure provides a host cell comprising the nucleic acid construct as herein defined.

In still another one of its aspects the present disclosure provides a host cell transfected with the vector as herein defined.

In some embodiments the cell according to the present disclosure is a eukaryotic cell.

In other embodiments the cell according to the present disclosure is a mammalian cell.

The present disclosure further provides a method for identifying a macrolide that induces read-through of a nonsense mutation, the method comprising:
  a. contacting a candidate macrolide with a population of cells containing a nucleic acid construct comprising: (i) an upstream nucleic acid sequence encoding a fluorescent protein selected from GFP and BFP; (ii) a downstream nucleic acid sequence encoding a fluorescent protein different from the upstream fluorescent protein and selected from GFP and BFP; and (iii) a nucleic acid sequence comprising a nonsense mutation associated with a genetic neurodegenerative or neurodevelopmental disease, interposed between the upstream and downstream nucleic acid sequences; wherein the upstream, downstream and interposed nucleic acid sequences are linked in-frame in a single ORF; and
  b. measuring the fluorescence of the downstream fluorescent protein;
  c. wherein an increase in the fluorescence level of the downstream fluorescent protein in the cells containing said nucleic acid construct contacted with said candidate macrolide compared to cells containing said nucleic acid construct and not contacted with said candidate macrolide is indicative that the candidate macrolide induces read-through of a nonsense mutation.

In some embodiments according to the present disclosure the upstream fluorescent protein is GFP and the downstream fluorescent protein is BFP.

In other embodiments the interposed nucleic acid sequence comprising a nonsense mutation according to the present disclosure is of at least 45 nucleotides.

In further embodiments the fluorescence of the downstream fluorescent protein is measured only in cells expressing both the upstream and downstream fluorescent proteins.

In still further embodiments the method for identifying a macrolide that induces read-through of a nonsense mutation according to the present disclosure comprises detecting or sorting cells expressing both the upstream and downstream fluorescent proteins.

In some embodiments the method for identifying a macrolide that induces read-through of a nonsense mutation according to the present disclosure is wherein an increase in the fluorescence level of the downstream fluorescent protein in the cells containing said nucleic acid construct contacted with said candidate macrolide compared to cells containing said nucleic acid construct and not contacted with said candidate macrolide of at least about 7-25% is indicative that the candidate macrolide is a suitable read-through agent for clinical applications.

In other embodiments the method for identifying a macrolide that induces read-through of a nonsense mutation according to the present disclosure is wherein measuring the fluorescence of the downstream fluorescent protein is performed by a fluorescence-activated cell sorter (FACS).

In further embodiments the method for identifying a macrolide that induces read-through of a nonsense mutation according to the present disclosure further comprised comparing the fluorescent level of the downstream fluorescent protein between cells containing the construct and contacted with the candidate macrolide to cells containing a control construct with no nonsense mutation.

In some embodiments the macrolide according to the present disclosure is an antibiotic macrolide.

In still another one of its aspects the present disclosure provides a method of treating a genetic neurodegenerative or neurodevelopmental disease resulting from or associated with a nonsense mutation comprising:

(i) selecting a nonsense mutation read-through macrolide for treating a subject in need thereof by a method comprising:
 a. identifying in a biological sample obtained from said subject at least one nonsense mutation in a gene associated with a genetic neurodegenerative or neurodevelopmental disease;
 b. providing a nucleic acid construct comprising a fragment of at least 45 nucleotides corresponding to said identified mutation of (a) and its surrounding nucleotides, flanked by two nucleic acid sequences encoding two distinct fluorescent proteins selected from GFP and BFP, wherein the fragment and the nucleic acid sequences encoding the two distinct fluorescent proteins are linked in-frame in a single ORF;
 c. introducing the construct of (b) into a host cell; and
 d. contacting the host cells containing the construct of (b) with a candidate read-through macrolide; and
 e. detecting the presence of read-through polypeptides containing both fluorescent proteins;
 f. wherein the presence of read-through polypeptides containing both fluorescent proteins is indicative that said candidate read-through macrolide is a nonsense mutation read-through macrolide; and (ii) administering said nonsense mutation read-through macrolide to said subject.

The present disclosure further provides a composition comprising at least one antibiotic macrolide in combination with at least one additional therapeutically effective, for use in a method of treating a genetic neurodegenerative or neurodevelopmental disease associated with a nonsense mutation in a patient in need thereof.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1 GFP-BFP plasmid construction

FIG. 1A is a schematic illustration of the screening plasmid termed the "GFP-C2-BFP" construct.

FIG. 1B presents immunofluorescence photographs of the GFP-C2-BFP construct, showing either blue fluorescence protein (BFP) fluorescence or green fluorescence protein (GFP) fluorescence in left panels or a merge of blue and green fluorescence originating in a fusion protein expressing both BFP and GFP proteins (right panels).

FIG. 1C presents schematic illustrations of the screening plasmid and corresponding cells distribution diagrams obtained by FACS analysis according to GFP and BFP emissions.

FIG. 1C-1 is a "WY" GFP-C2-BFP plasmid construct expressing both GFP and BFP.

FIG. 1C-2 is a GFP-C2-BFP plasmid construct comprising a nonsense mutation and expresses only GFP.

FIG. 1C-3 is a GFP-C2-BFP plasmid construct comprising a nonsense mutation which is being read-through in the presence of erythromycin.

FIG. 1D presents an overlay illustration of FACS data obtained in the presence of different concentrations of antibiotic macrolide treatment, where the shift in mean values represents degree of read-through.

Abbreviations: WT, wild type; mut, mutation; GFP, green fluorescent protein; BFP, blue fluorescent protein; Ery, erythromycin.

Figures 1, 1C, 2, 3:
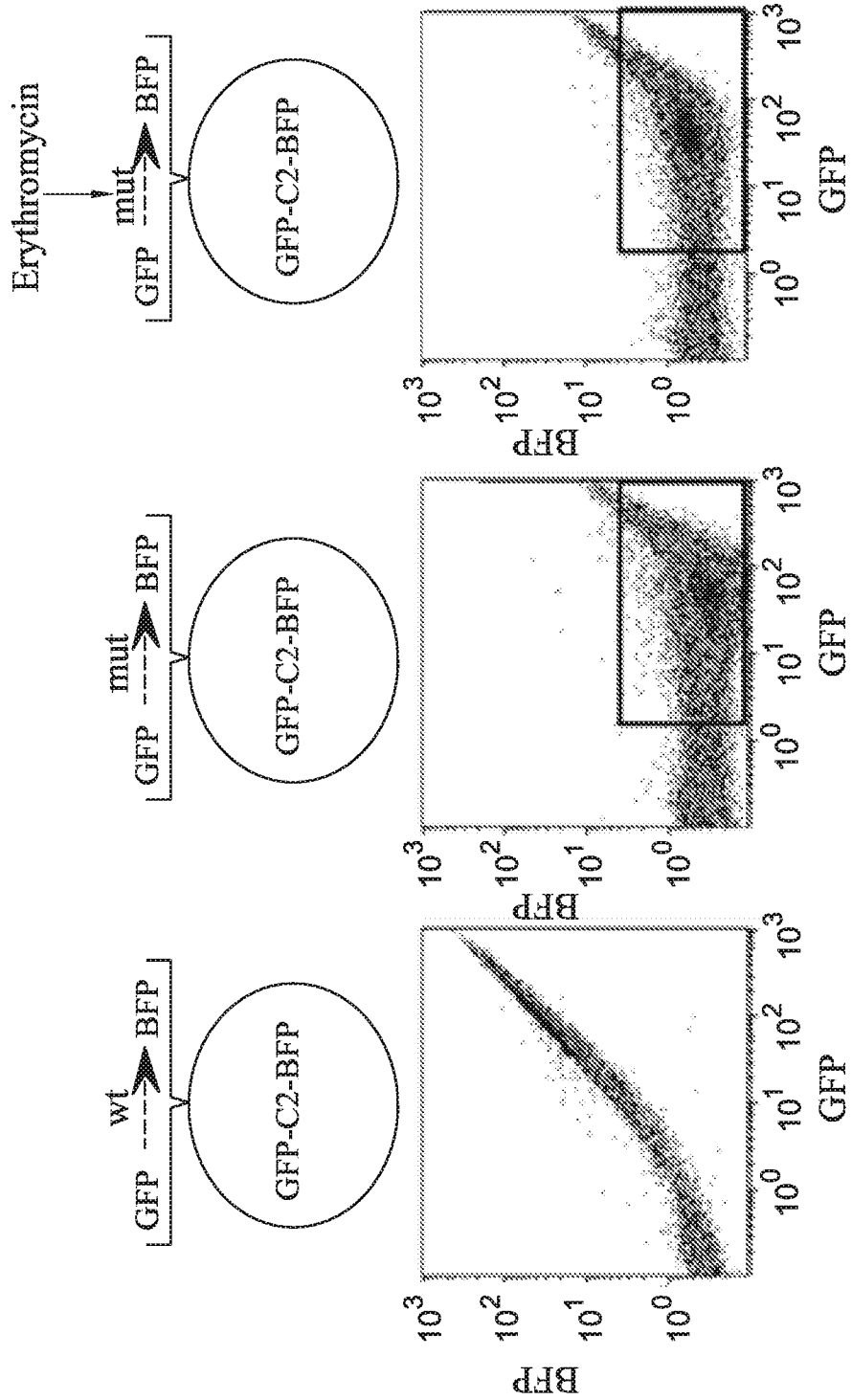

FIG. 2 Effect of different erythromycin doses on read-through of the ATM mutation A bar graph showing the normalized fluorescence readings (MFI) obtained for HEK293T cells transfected with the GFP-C2-BFP plasmid comprising an ATM nonsense mutation (namely, the TGA stop codon) and incubated in the presence of 0, 300, 500 or 700 μg/ml erythromycin for 24, 36 or 48 hours.

FIG. 3 ATM protein restoration

Figure 3A:
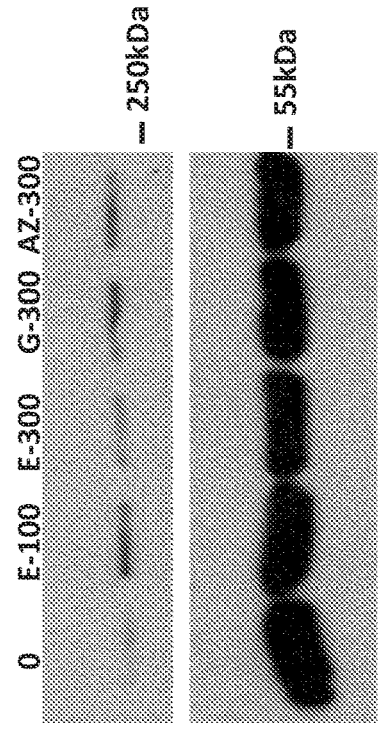

FIG. 3A is a Western blot analysis of B-lymphocytes obtained from Ataxia telangiectasia (A-T) patients carrying a heterozygous nonsense mutation C5515→T, which were incubated in the presence of the indicated antibiotics (at 300 μg/ml) for 7 days, in comparison to WT B-lymphocytes. Cells were harvested and subjected to SDS-PAGE and Western blot analysis using specific anti-ATM antibodies.

Figure 3D:
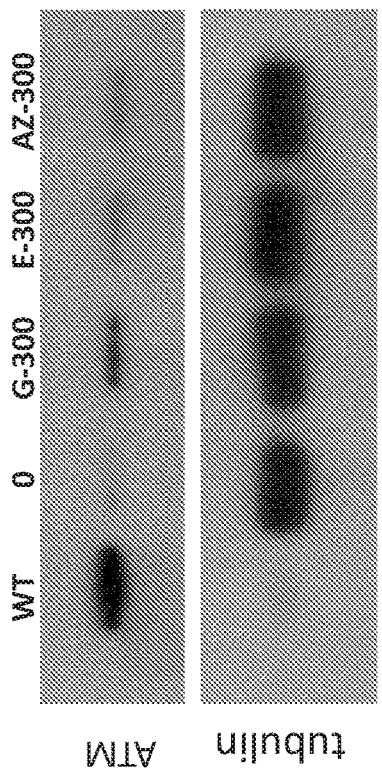
Figure 3B:
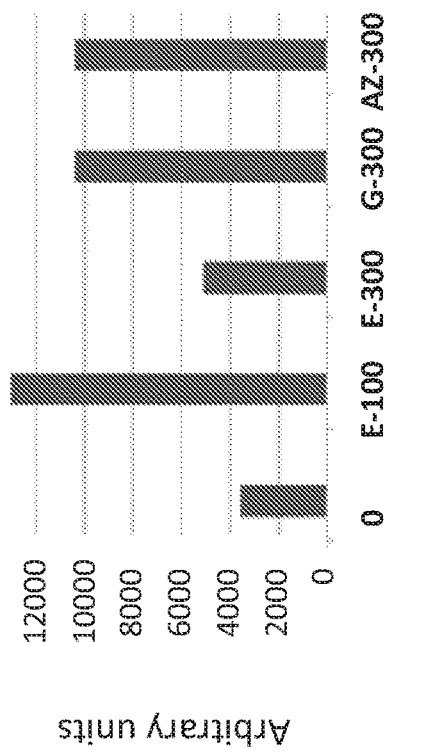

FIG. 3B is a Western blot analysis of B-lymphocytes obtained from Ataxia telangiectasia (A-T) patients carrying a heterozygous nonsense mutation C5515→T, which were incubated in the presence of the indicated antibiotics (at 100 or 300 μg/ml) for 7 days. Cells were harvested and subjected to SDS-PAGE and Western blot analysis using specific anti-ATM antibodies.

Figure 3C:
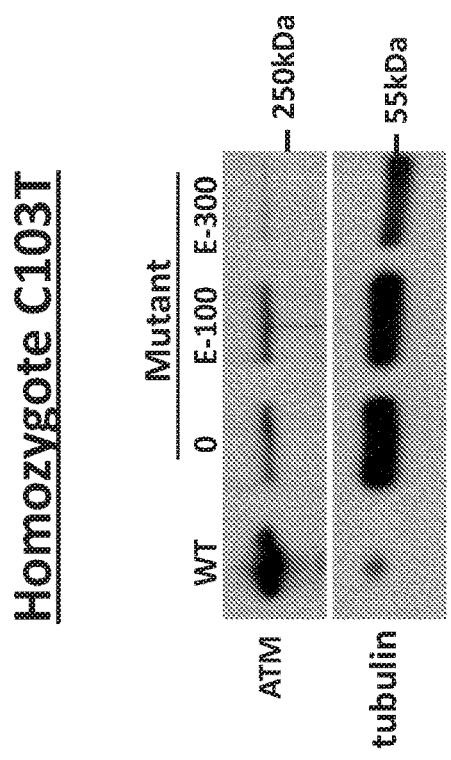

FIG. 3C is a bar graph representing the band intensity shown in FIG. 3B that was analyzed by the TINA software.

FIG. 3D is a Western blot analysis of homozygous A-T mutant C103→T and WT cells treated with the indicated antibiotics for 7 days. Cells were then harvested and subjected to SDS-PAGE and Western blot analysis using specific anti-ATM antibodies.

Abbreviations: 0, no treatment; E, Erythromycin; AZ, Azithromycin; G, Gentamycin Sulfate, WT, wild type.

Figure 4A:
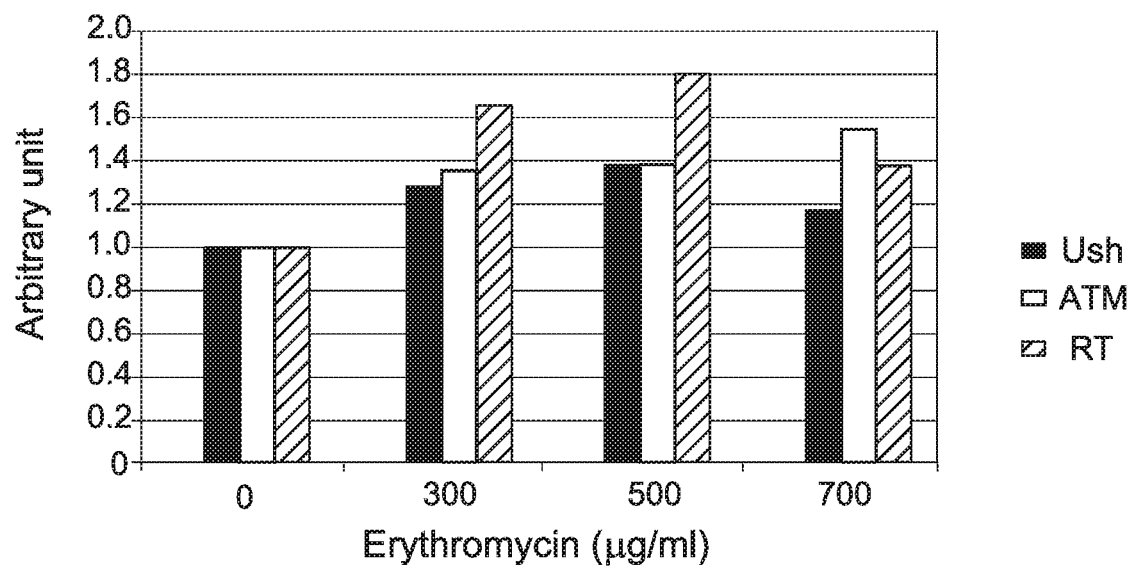
Figure 4B:
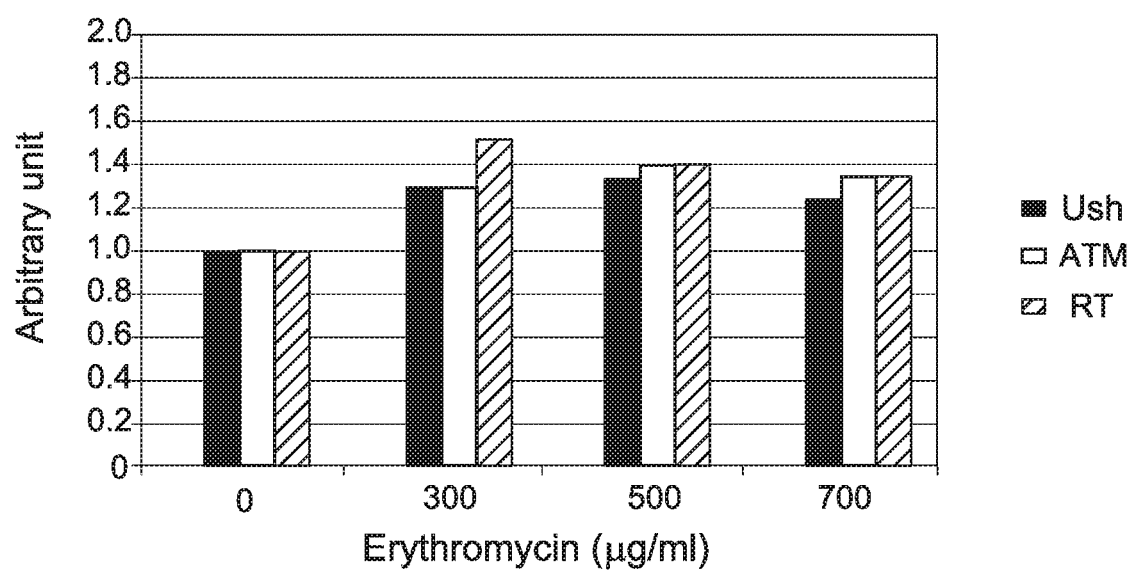

FIG. 4 Effect of different erythromycin doses on read-through of nonsense mutations Bar graphs showing the effect of erythromycin at 0, 300, 500 or 700 μg/ml on the read-through of nonsense mutations in nucleic acid fragments of the genes associated with Usher syndrome ("Ush"/"U"), Rett syndrome ("RT"/"R") and ataxia telangiectasia ("ATM"/"A") upon incubation of HEK293T cells transfected with the GFP-C2-BFP plasmid comprising the corresponding nonsense mutation and incubated in the presence of the indicated erythromycin concentration for 24 hours (FIG. 4A) or 48 hours (FIG. 4B).

Figure 5:
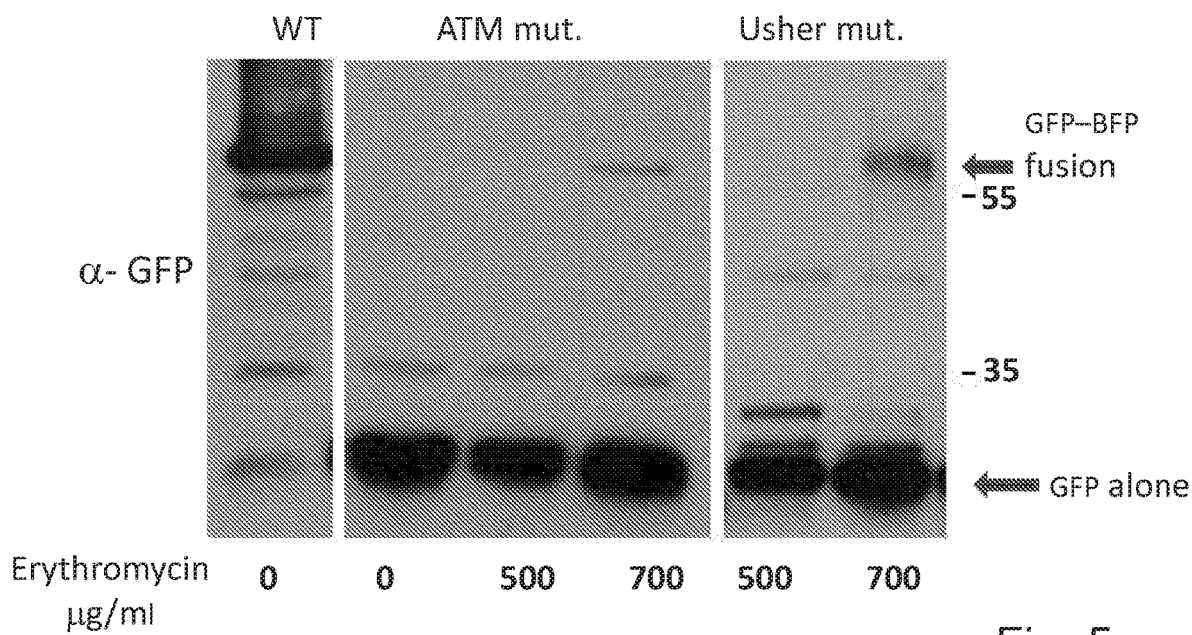

FIG. 5 Expression of full length protein Western blot analysis of erythromycin effect at 0, 500 or 700 μg/ml on read-through of nonsense mutations associated with ataxia telangiectasia ("ATM mut.") and Usher syndrome ("Usher mut.").

Figure 6:
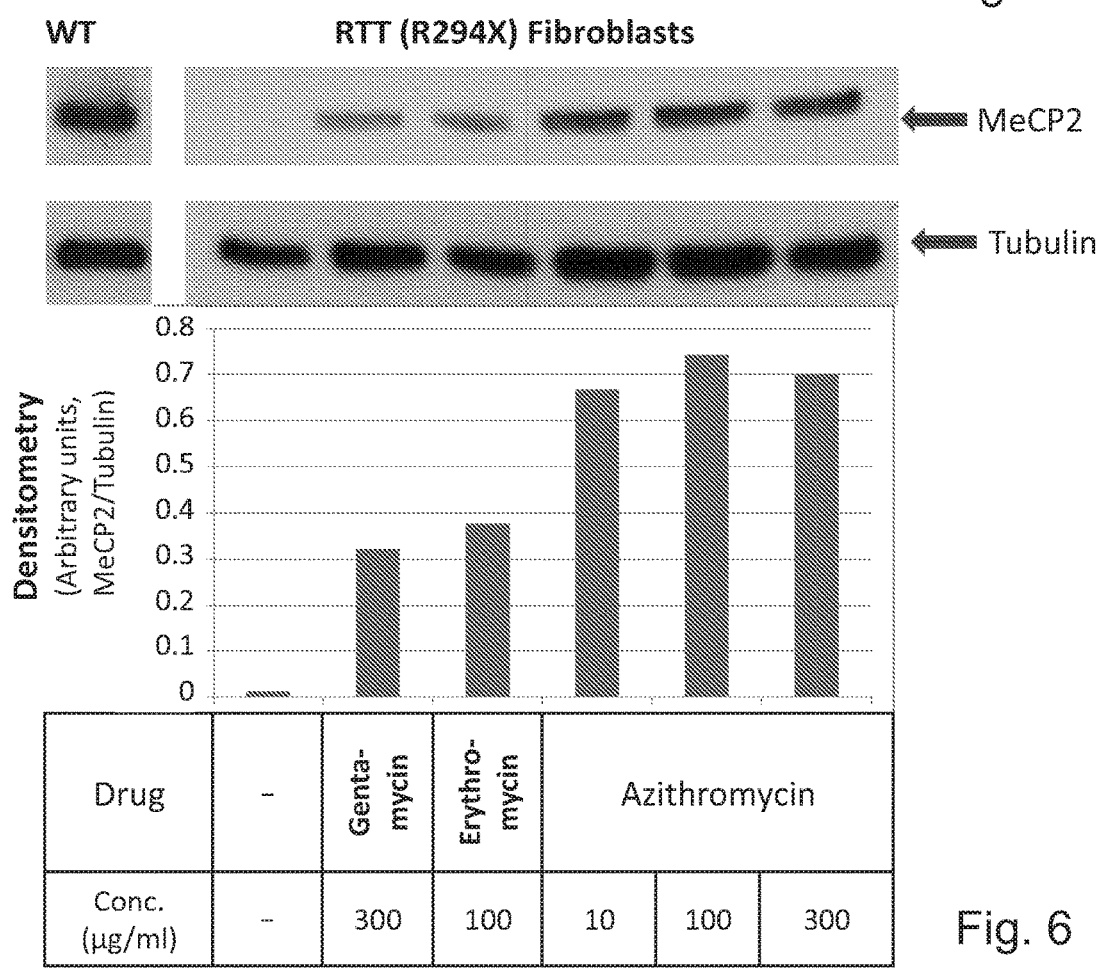

FIG. 6 Western blot analysis of RTT-R294X patient's fibroblasts

The upper panels shows a Western blot analysis of RTT-R294X patient's fibroblasts incubated for 7 days in the presence of Gentamicin (300 μg/ml), Erythromycin (100 μg/ml), Azithromycin (10, 100 or 300 μg/ml) or in their absence (−) using an anti-MeCP2 antibody. The expression level of MeCP2 in WT fibroblasts is presented for comparison (WT, left lane). The lower panel is a bar graph representing the band intensity of the blot analysis that was analyzed by the TINA software.

FIG. 7 Nucleus localization of MeCp2

FIG. 7A shows staining of wild type (WT) fibroblasts with antibodies directed to MeCP2 (upper panel) or dapi (lower panel).

FIG. 7B is MeCp2 (upper panels) or dapi (lower panels) staining of fibroblasts that were incubated for 7 days in the presence of Gentamicin (300 µg/ml) or Erythromycin (100 µg/ml), or in their absence ("no drug", left panels), as indicated. The arrows indicate localization of the MeCp2 protein to the nucleus.

FIG. 7C is MeCp2 (upper panels) or dapi (lower panels) staining of fibroblasts that were incubated for 7 days in the presence of Azithromycin (10, 100 or 300 µg/ml), as indicated. The arrows indicate localization of the MeCp2 protein to the nucleus.

Figure 7D:
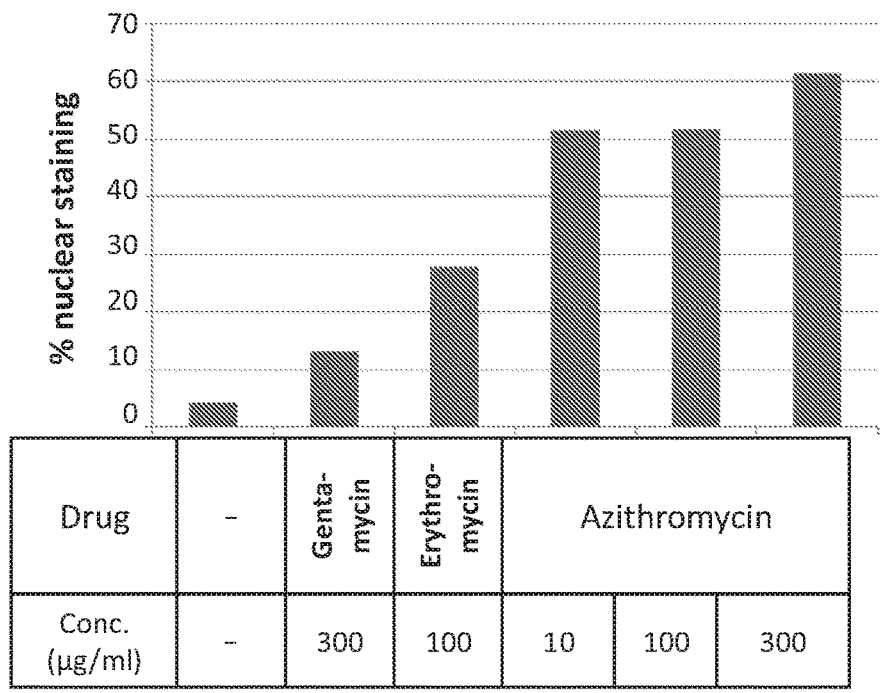

FIG. 7D is a bar graph representing nuclear staining percentage in 40-50 cells of each of the cells presented in FIG. 7B and FIG. 7C.

Abbreviations: WT, wild type; RTT, Rett syndrome; conc, concentration.

FIG. 8 Restoring SMN2 expression using macrolides

Figure 8A:
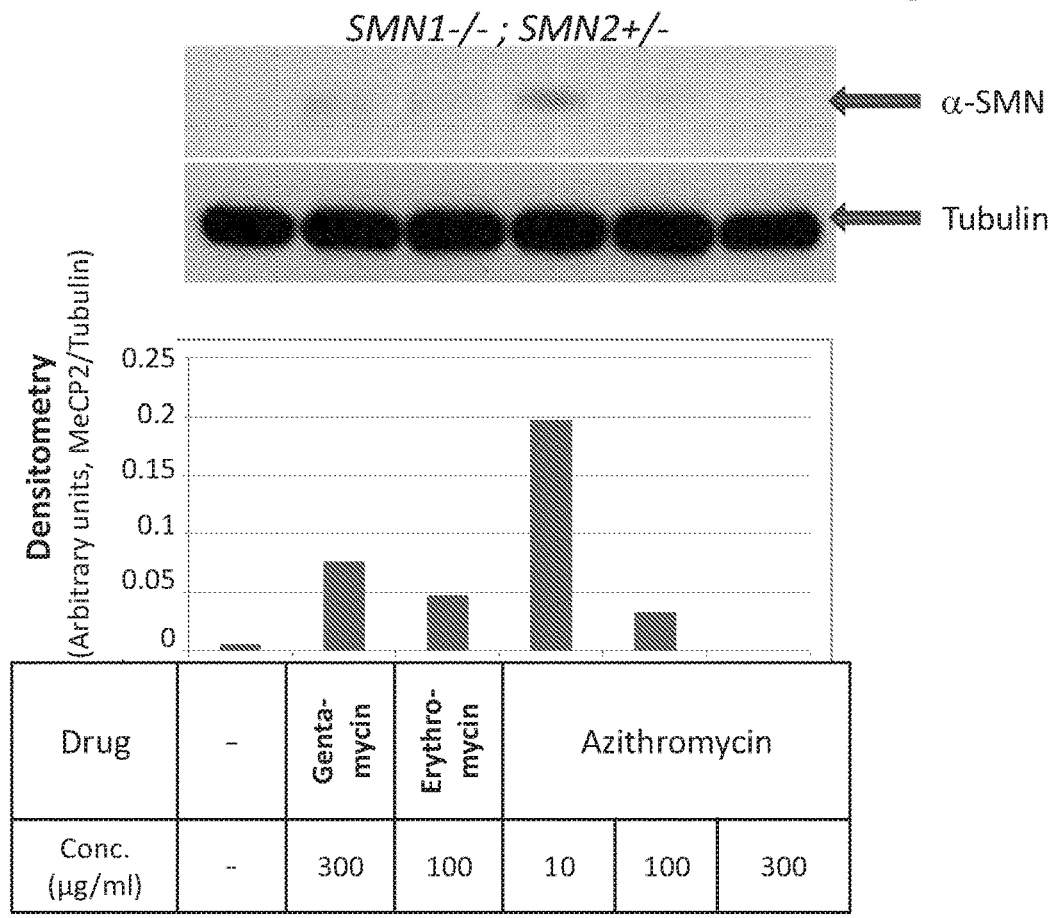

FIG. 8A (upper panel) is a Western blot analysis using anti-SMN antibody of SMA patient's fibroblasts (SMN1−/−; SMN2+/−) incubated 7 days in the presence of Gentamycin (300 µg/ml), Erythromycin (100 µg/ml), Azithromycin (10, 100 or 300 µg/ml) or in their absence (−), as indicated. The lower panel is a bar graph showing a quantification of the results shown in the upper panel.

Figure 8B:
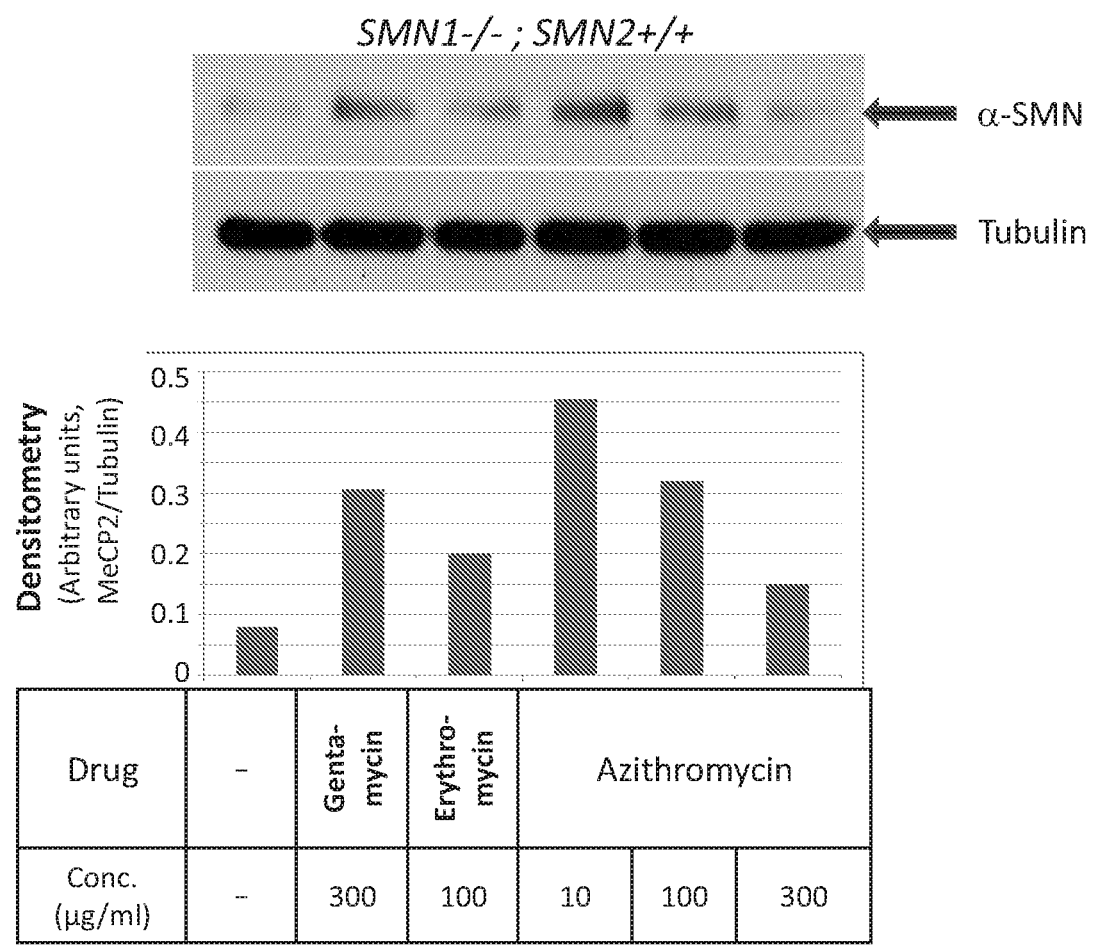

FIG. 8B (upper panel) is a Western blot analysis using anti-SMN antibody of SMA of patient's fibroblasts (SMN1−/−; SMN2+/+) incubated 7 days in the presence of Gentamycin (300 vg/ml), Erythromycin (100 µg/ml), Azithromycin (10, 100 or 300 µg/ml) or in their absence (−), as indicated. The lower panel is abar graph showing a quantification of the results shown in the upper panel.

Figure 8C:
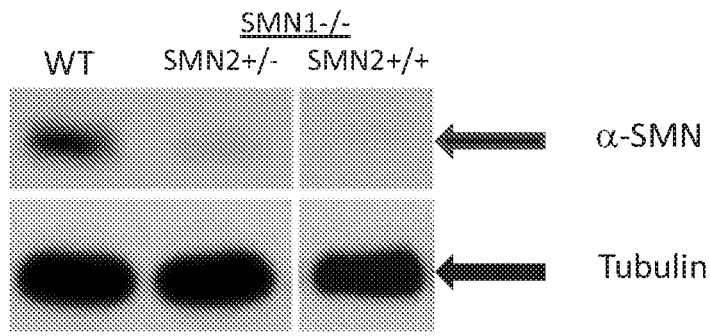

FIG. 8C is a Western blot analysis using anti-SMN antibody of SMA of patient's fibroblasts SMN1−/−; SMN2+/− or SMN1−/−; SMN2+/+ in the absence of any treatment.

Figure 8D:
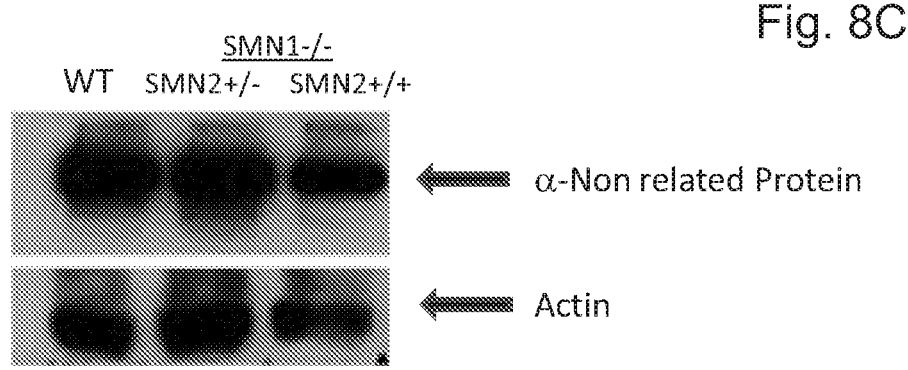

FIG. 8D is a Western blot analysis using antibodies directed to a non-relevant protein of SMA of patient's fibroblasts SMN1−/−; SMN2+/− or SMN1−/−; SMN2+/+ incubated for 7 days in the presence of Gentamycin or Erythromycin (each at 500 µg/ml) or in their absence, as a control assay.

Figure 8E:
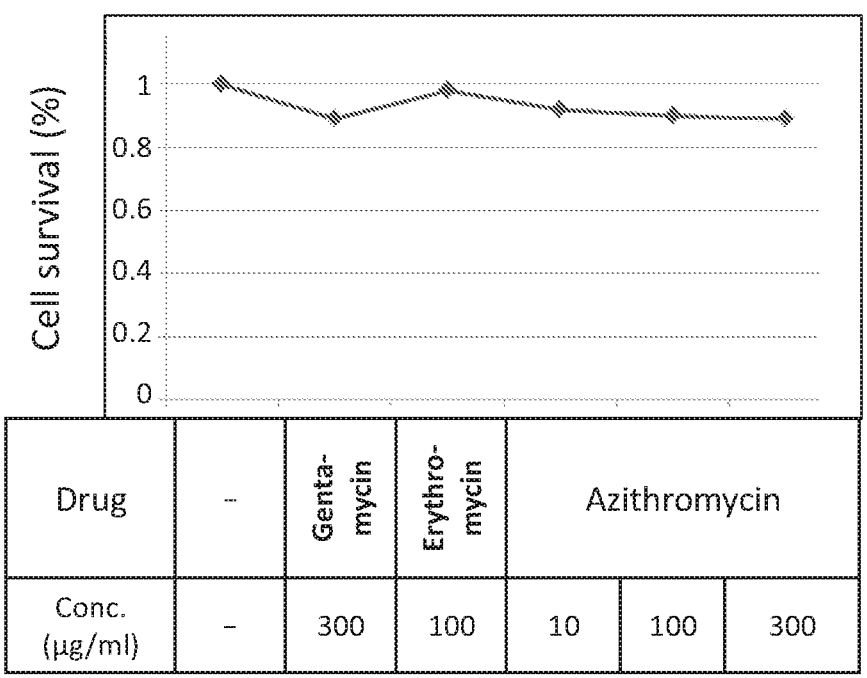

FIG. 8E is a graph showing cell survival following drug treatment (as indicated) of SMA fibroblasts (SMN1−/−; SMN2+/+), using the Alamar blue assay.

Abbreviations: SMN1, survival motor neuron 1; SMN2, survival motor neuron 2; conc, concentration.

DETAILED DESCRIPTION OF THE INVENTION

The present disclosure provides compositions and methods useful for treating genetic neurodegenerative or neurodevelopmental diseases resulting from nonsense mutations that lead to the formation of premature termination codons and consequently truncated, non-functional proteins.

The compositions and methods of the present disclosure utilize molecules of the antibiotic macrolide family that were surprisingly found to successfully induce read-through of mutated nucleic acid sequences associated with genetic neurodegenerative or neurodevelopmental diseases, as exemplified herein below.

Advantageously, even low levels of read-through, namely, low levels of translation of a full length functional protein, are expected to be of clinical significance to a patient suffering from a genetic neurodegenerative or neurodevelopmental disease. In other words restoring production of even modest amounts of a full length functional protein by read-through translation can be physiologically relevant, and symptoms or conditions associated with the genetic neurodegenerative or neurodevelopmental diseases may be largely improved.

The present disclosure further provides highly effective compositions and sensitive methods for identifying agents, for example macrolides or antibiotic macrolides that are capable of inducing nonsense mutation read-through. The read-through agents which are identified by the methods disclosed herein may be utilized for the treatment of genetic neurodegenerative or neurodevelopmental diseases resulting from nonsense mutations, such as the diseases described herein below.

Thus in one of its aspects the present disclosure provides a composition comprising at least one antibiotic macrolide for use in a method of treating a genetic neurodegenerative or neurodevelopmental disease associated with a nonsense mutation in a patient in need thereof.

The term "genetic neurodegenerative disease or neurodevelopmental disease associated with a nonsense mutation" as herein defined encompasses any genetic neurodegenerative or neurodevelopmental disease that results from or is associated with a nonsense mutation in a certain gene, namely, a mutation that introduces a premature stop codon (also referred to as a premature termination codon) in the nucleic acid sequence of a specific gene.

Many genetic neurodegenerative or neurodevelopmental diseases are known to be associated, at least partially, with nonsense mutations or with premature stop codons in specified locations in genes encoding specific proteins, which lead to the production of a truncated (or incomplete) and usually nonfunctional protein product. As used herein, "genetic neurodegenerative or neurodevelopmental diseases resulting from a premature termination codon" or "genetic neurodegenerative or neurodevelopmental diseases resulting from a nonsense mutation" are used interchangeably and refer to diseases for which a nonsense mutation, which leads to the formation of a truncated protein, has been identified as one of the underlying factors causing the disease. It is to be understood that the term "resulting" does not indicate that the nonsense mutation is the only factor that causes the disease.

The term "nonsense mutation" as herein defined is a mutation in a nucleic acid sequence that results in a premature stop codon, or a nonsense codon in the transcribed mRNA, and consequently in a truncated, or incomplete, and usually nonfunctional protein product. In other words, a "nonsense mutation" is a mutation changing a codon corresponding to an amino acid to a stop codon.

The term "stop codon" (also referred to as termination codon) is a nucleotide triplet within messenger RNA that signals termination of translation, as opposed to most codons in messenger RNA that correspond to the addition of an amino acid residue to a growing polypeptide chain.

Thus the term "premature termination codon" or "premature stop codon" as known in the art refers to the occurrence of a stop codon instead of a codon corresponding to an amino acid residue. The premature stop codon may be located anywhere upstream to the normal stop codon which is regularly located at the end of the coding nucleic acid sequence of a particular gene.

The premature termination codon may be any one of the known stop codons, including TAG (transcribed as UAG), TAA (transcribed as UAA) and TGA (transcribed as UGA). Each possibility represents a distinct embodiment of the invention.

In some embodiments the premature termination codon is TGA (transcribed as UGA).

As shown below, effective read-through of a protein was obtained for cells treated with antibiotic macrolides at a dose range of 10-100 μg/ml, for example as demonstrated in FIG. 6 for R294X fibroblasts incubated in the presence of 10-100 μg/ml azithromycin.

Measuring the levels of macrolide azithromycin in brain tissue, CSF and eye humor, Jaruratanasirikul et al. (21) reported that following 500 mg oral administration, the concentration of azithromycin in non-infected humans was at the range of 0.008 to 0.031 μg/ml in serum and undetected to 0.015 μg/ml in the CSF. For effective treatment of genetic neurodegenerative or neurodevelopmental disease associated with a nonsense mutation, concentrations of about 10 μg/ml macrolide in the CSF should be aimed at. These concentrations cannot be achieved through i.v. or oral route administration, because this will require a dose which is 666-fold higher than the current approved dose of 10 mg/kg i.v. (for example of azithromycin). If Azithromycin was to be administered at 10 mg/kg intravenous (i.v.), which is the highest approved dose as an antibiotic agent, upon its distribution in the body, the effective concentration of Azithromycin in the CSF would only be about 0.3 μg/ml, which is apparently outside the range of effective read-through, as mentioned above. Hence the only safe and nontoxic route of administration in order to achieve a therapeutically effective dosage in the CSF would be a non systemic administration of the antibiotic macrolide, for example, but not limited to a direct injection into the central nervous system (CNS).

In addition, systemic administration of antibiotic in general and antibiotic macrolide in particular have various side effects, for example, destruction of bacterial flora in the body, which is beneficial to digestion and the formation of mutated bacterial strains to name but few.

Thus, by another one of its aspects the present disclosure provides a composition comprising at least one antibiotic macrolide for use in a method of treating a genetic neurodegenerative or neurodevelopmental disease associated with a nonsense mutation in a patient in need thereof, wherein said composition is administered non-systemically.

The term "non-systemically" as herein defined refers to a local route of administration, namely a route of administration which is not via the digestive tract and not parenterally.

Administration can be chronic repeated administration to a patient in need. By "chronic repeated administration" as used herein is meant giving a measure quantity of the macrolide antibiotic agent on a regular basis to a patient. The regular basis can be, for example, once daily, once every other day, twice a week, weekly, once in consecutive two weeks, once a month or once every two consecutive months. Administration and doses are determined by good medical practice of the attending physician and may depend on the age, sex, weight and general condition of the patient.

The present disclosure is based on the surprising finding that antibiotic macrolides are capable of inducing read-through of nonsense mutations in various genes associated with genetic neurodegenerative or neurodevelopmental diseases, for example as shown in examples 2 and 3 below for the disease Ataxia telangiectasia, where the antibiotic macrolide erythromycin was able to induce read-through of the premature stop codon found in the gene encoding the Ataxia telangiectasia mutated (ATM) protein.

As used herein, the term "read-through", when referring to the process of translation, means reading a stop codon ("nonsense" codon) as a "sense" codon (i.e., a codon which codes for an amino acid) or bypassing said stop codon, thereby restoring, at least partially, the synthesis of a full length protein.

It is important therefore to identify agents that can induce read-through.

Therefore in yet another aspect the present disclosure provides a composition comprising at least one antibiotic macrolide for use in a method of treating a genetic neurodegenerative or neurodevelopmental disease associated with a nonsense mutation in a patient in need thereof, wherein said composition is administered non-systemically and wherein said at least one antibiotic macrolide induces read-through of said nonsense mutation.

The term "induces read-through of said nonsense mutation" as used herein refers to at least a partial increase, production, increment or rise in the translation of a full length protein which is encoded by a nucleic acid sequence comprising a nonsense mutation (also referred to herein as a premature stop codon). Said increase in the translation of a full length protein may be by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or about 100%.

As exemplified below, the present disclosure is based on the use of a nucleic acid constructs and screening methods which enable the identification and selection of agents such as macrolides or antibiotic macrolides that induces read-through of said nonsense mutation.

The nucleic acid constructs disclosed herein comprise a nucleic acid sequence encoding a green-fluorescence-protein (GFP) and a nucleic acid sequence encoding a blue-fluorescence-protein (BFP) separated by an oligonucleotide that contains a nonsense mutation. The oligonucleotide that contains a nonsense mutation corresponds to a mutated fragment of a gene that is known to underlie a certain genetic neurodegenerative or neurodevelopmental disease. The nucleic acid constructs in accordance with the present disclosure are schematically presented for example in FIG. 1A, where the oligonucleotide that contains a nonsense mutation is presented as a dotted line.

As used herein by the term "corresponds" it is meant that the sequence of the oligonucleotide containing a nonsense mutation is homologous to a fragment of a gene that encodes a protein which is known to be defective due to a nonsense mutation in said gene and underlies a certain genetic neurodegenerative or neurodevelopmental disease, where the fragment spans the region of the gene that includes the nonsense mutation, namely it includes a premature stop codon.

Translation of the region encoding the fluorescent protein located downstream to the nucleic acid sequence comprising the nonsense mutation can only be induced by the readthrough agent, for example in the presence of an antibiotic macrolide as shown herein below.

As exemplified below in FIG. 4A and in FIG. 4B, the fluorescence intensity of BFP, the fluorescent protein located downstream to the nucleic acid sequence comprising the nonsense mutation, increased in the presence of erythromycin, demonstrating the ability of erythromycin to facilitate read-through of the complete fusion protein comprising GFP and BFP in a variable context of nucleic acid sequences, for example as demonstrated in example 5 for genes associated with Usher syndrome and Rett syndrome.

The ability of an agent, for example a macrolide or an antibiotic macrolide compound to induce read-through can be tested using the assays described herein and exemplified in the Examples section herein below.

Thus, in an embodiment of the presently disclosed subject matter, provided is a composition comprising at least one antibiotic macrolide for use in a method of treating a genetic neurodegenerative or neurodevelopmental disease associated with a nonsense mutation in a patient in need thereof, wherein said composition is administered non-systemically and wherein said at least one antibiotic macrolide induces read-through of said nonsense mutation and is identified by the method comprising:

a. contacting a candidate antibiotic macrolide with a population of cells containing a nucleic acid construct comprising: (i) an upstream nucleic acid sequence encoding a fluorescent protein selected from GFP and BFP; (ii) a downstream nucleic acid sequence encoding a fluorescent protein different from the upstream fluorescent protein and selected from GFP and BFP; and (iii) a nucleic acid sequence comprising a nonsense mutation associated with said genetic neurodegenerative or neurodevelopmental disease, interposed between the upstream and downstream nucleic acid sequences; wherein the upstream, downstream and interposed nucleic acid sequences are linked in-frame in a single ORF; and b. measuring the fluorescence of the downstream fluorescent protein;

wherein an increase in the fluorescence level of the downstream fluorescent protein in the cells containing said nucleic acid construct contacted with said candidate antibiotic macrolide compared to cells containing said nucleic acid construct and not contacted with said candidate antibiotic macrolide is indicative that the candidate antibiotic macrolide induces read-through of said nonsense mutation.

The read-through agent so identified constitutes the active ingredient in the composition.

As indicated above the only safe and nontoxic route of administration in order to achieve a therapeutically effective dosage in the CSF would be a non systemic administration of the antibiotic macrolide, for example, but not limited to a direct injection into the central nervous system (CNS).

Therefore in some embodiments of the presently disclosed subject matter, the composition as herein defined is directly administered to the CNS in a therapeutically effective dose.

In other words, in an embodiment of the presently disclosed subject matter, provided is a composition comprising at least one antibiotic macrolide for use in a method of treating a genetic neurodegenerative or neurodevelopmental disease associated with a nonsense mutation in a patient in need thereof, wherein said composition is directly administered to the CNS in a therapeutically effective dose and wherein said at least one antibiotic macrolide induces read-through of said nonsense mutation and is identified by the method comprising:

a. contacting a candidate antibiotic macrolide with a population of cells containing a nucleic acid construct comprising: (i) an upstream nucleic acid sequence encoding a fluorescent protein selected from GFP and BFP; (ii) a downstream nucleic acid sequence encoding a fluorescent protein different from the upstream fluorescent protein and selected from GFP and BFP; and (iii) a nucleic acid sequence comprising a nonsense mutation associated with said genetic neurodegenerative or neurodevelopmental disease, interposed between the upstream and downstream nucleic acid sequences; wherein the upstream, downstream and interposed nucleic acid sequences are linked in-frame in a single ORF; and b. measuring the fluorescence of the downstream fluorescent protein;

wherein an increase in the fluorescence level of the downstream fluorescent protein in the cells containing said nucleic acid construct contacted with said candidate antibiotic macrolide compared to cells containing said nucleic acid construct and not contacted with said candidate antibiotic macrolide is indicative that the candidate antibiotic macrolide induces read-through of said nonsense mutation.

As indicated above, even low levels of translation of a full length functional protein are expected to be of clinical significance to a patient suffering from a genetic neurodegenerative or neurodevelopmental disease.

Therefore in another one of its aspects the present disclosure provides a composition comprising at least one antibiotic macrolide for use in at least partially restoring production of an intra-cellular or subcellular functional protein, thereby treating at least one symptom or condition of a genetic neurodegenerative or neurodevelopmental disease associated with production of said intra-cellular or subcellular protein in a non-functional form resulting from at least one nonsense mutation.

By the term "at least partially restoring production" or "restoring at least partial production" is meant at least a partial increase, increment or rise in the production (translation) of an intra-cellular or subcellular functional protein, namely translation of a full length protein associated with a genetic neurodegenerative or neurodevelopmental disease. Said increase, increment or rise in the production of an intra-cellular functional protein may be by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or about 100%.

By the term "intra-cellular or subcellular functional protein" it is meant a full length protein associated with a genetic neurodegenerative or neurodevelopmental disease, which has proper biological function and which is produced inside the cell or in a compartment thereof.

By the term "at least one symptom or condition of a genetic neurodegenerative or neurodevelopmental disease" it is meant disorders of gait, movement and coordination, muscle weakness, sensory disorders impaired cognition and intellectual capabilities.

Thus, in an embodiment of the presently disclosed subject matter, provided is a composition comprising at least one antibiotic macrolide for use in at least partially restoring production of an intra-cellular or subcellular functional protein, thereby treating at least one symptom or condition of a genetic neurodegenerative or neurodevelopmental disease associated with production of said intra-cellular or subcellular protein in a non-functional form resulting from at least one nonsense mutation, wherein said composition is directly administered to the CNS in a therapeutically effective dose.

In some embodiments of the presently disclosed subject matter said at least partially restoring production of said intra-cellular functional protein is at least 7% production of functional protein, of total protein produced.

In other embodiments of the presently disclosed subject matter said at least partially restoring production of said intra-cellular functional protein is between about 7% to about 25% production of functional protein, of total protein produced.

In other words, the composition presently disclosed comprising an antibiotic macrolide may be effective in restoring at least partially, namely in the range of between about 7% to about 25% the translation of a full length intra-cellular or subcellular functional protein.

The term "macrolides" as herein defined refers to a group of drugs (typically antibiotics) whose activity stems from the presence of a macrolide ring, a large macrocyclic lactone ring to which one or more deoxy sugars, usually cladinose and desosamine, may be attached. The lactone rings are usually 14-, 15-, or 16-membered. Macrolides belong to the polyketide class of natural products. The term macrolide as used herein also encompasses salts, derivatives and analogues of the same.

Macrolides in accordance with the present disclosure include azalide, azithromycin, boromycin, brefeldin, candicidin, clarithromycin, dirithromycin, erythromycin, fidaxomicin, filipin, flopristin, flurithromycin, josamycin, kitasamycin, macrocin, mepartricin, midecamycin, miocamycin, nargenicin, oleandomycin, oligomycin, pentamycin, pikromycin, pristinamycin iia, pristinamycin iib, rokitamycin, roxithromycin, solithromycin, spiramycin, streptogramin a, streptovaricin, tilmicosin, troleandomycin, tulathromycin, tylosin and virginiamycin.

As used herein, the term "derivative", when referring to a macrolide compound, refers to a chemically modified compound derived from a parent compound that differs from the parent compound by one or more elements, substituents and/or functional groups such that the derivative has the same or similar biological properties/activities as the parent compound such as defined herein.

As exemplified below, the inventors have shown that the macrolides erythromycin, and azithromycin are effective in restoring translation of a full length protein, namely are effective as read-through agents.

The term "antibiotic macrolide" as herein defined thus refers to a macrolide with an antibiotic activity, for example by not limited to Azithromycin, Clarithromycin, Dirithromycin, Erythromycin, Roxithromycin, Telithromycin, Carbomycin A, Josamycin, Kitasamycin, Midecamycin/midecamycin acetate, Oleandomycin, Solithromycin, Spiramycin, Troleandomycin and Tylosin/tylocine.

Thus in some embodiments of the presently disclosed subject matter the composition as herein described comprises at least one macrolide selected from a group consisting of erythromycin, azithromycin and clarithromycin or any combination of at least two thereof.

The macrolide compounds or salts thereof utilized according to embodiments of the present invention are commercially available, and may also be synthesized using methods known in the art.

In some embodiments, the macrolide is erythromycin. Erythromycin may be identified by CAS registry number 114-07-8. Examples of erythromycin salts and derivatives include, without limitation, erythromycin lactobionate, erythromycin ethylsuccinate, erythromycin stearate, erythromycin estolate, erythromycin estorate, erythromycin acistrate, erythromycin gluceptate, erythromycin propionate, erythromycin salnacedin, erythromycin A, B, C, D, or E, roxithromycin, clarithromycin, azithromycin, dirithiOmycin, flurithromycin, as well as derivatives such as those shown in U.S. Pat. Nos. 6,777,543, 6,825,171, and 5,602, 106, and WO2002/050093.

In some embodiments, the macrolide is azithromycin. Azithromycin may be identified by CAS registry number 83905-01-5. Its structure and antibiotic activity have been disclosed, for example in U.S. Pat. Nos. 4,474,768 and 4,517,359.

In some embodiments, the macrolide is clarithromycin. Clarithromycin may be identified by CAS registry number 81103-11-9. Its structure and antibiotic activity have been disclosed, for example in U.S. Pat. No. 4,331,803.

As indicated above, the composition in accordance with the present disclosure may be administered directly to the CNS.

As herein defined the term "central nervous system" (CNS) is defined as the part of the nervous system which in vertebrates consists of the brain and spinal cord, to which sensory impulses are transmitted and from which motor impulses pass out, and which coordinates the activity of the entire nervous system Examples of direct administration into the CNS include intrathecal administration (introduction of the therapeutic substance into the subarachnoid space of the spinal cord so that it reaches the cerebrospinal fluid), and direct administration into the brain, such as intra-cerebral, intra-ventricular, intra cranial routes of administration. Such routes of administration may be particularly beneficial for diseases affecting the central nervous system.

Thus in the above and other embodiments the composition according to the present disclosure is administered in a route of administration selected from the group consisting of intrathecal, intraneural, intra-cerebral, intra-ventricular and intra-cranial.

In some embodiments the composition according to the present disclosure is administered intrathecally.

In other words, in an embodiment of the presently disclosed subject matter, provided is a composition comprising at least one antibiotic macrolide for use in a method of treating a genetic neurodegenerative or neurodevelopmental disease associated with a nonsense mutation in a patient in need thereof, wherein said composition is administered intrathecally in a therapeutically effective dose and wherein said at least one antibiotic macrolide induces read-through of said nonsense mutation and is identified by the method comprising:

a. contacting a candidate antibiotic macrolide with a population of cells containing a nucleic acid construct comprising: (i) an upstream nucleic acid sequence encoding a fluorescent protein selected from GFP and BFP; (ii) a downstream nucleic acid sequence encoding a fluorescent protein different from the upstream fluorescent protein and selected from GFP and BFP; and (iii) a nucleic acid sequence comprising a nonsense mutation associated with said genetic neurodegenerative or neurodevelopmental disease, interposed between the upstream and downstream nucleic acid sequences; wherein the upstream, downstream and interposed nucleic acid sequences are linked in-frame in a single ORF; and b. measuring the fluorescence of the downstream fluorescent protein;

wherein an increase in the fluorescence level of the downstream fluorescent protein in the cells containing said nucleic acid construct contacted with said candidate antibiotic macrolide compared to cells containing said nucleic acid construct and not contacted with said candidate antibiotic macrolide is indicative that the candidate antibiotic macrolide induces read-through of said nonsense mutation.

As exemplified in the examples below, the inventors have shown that translation of the full length protein MeCP2 associated with the disease Rett syndrome and of the full length protein ATM associated with the disease ataxia-telangiectasia were obtained upon incubation of cells harboring a stop codon in genes encoding these proteins in the presence of erythromycin or azythromycin (see for example FIG. 6 and FIG. 3, respectively).

Thus in all embodiments and aspects of the presently disclosed subject matter the genetic neurodegenerative or neurodevelopmental disease can be Spinal Muscular Atrophy, Ataxia-telangiectasia, Rett syndrome, Usher syndrome, a peroxisome biogenesis disorder, Hurler syndrome, lysosomal storage disease, Activator Deficiency/GM2 Gangliosidosis, Alpha-mannosidosis, Aspartylglucosaminuria, Cholesteryl ester storage disease, Chronic Hexosaminidase A Deficiency, Cystinosis, Danon disease, Fabry disease, Farber disease, Fucosidosis, Galactosialidosis, Gaucher Disease, GM1 gangliosidosis, I-Cell disease/Mucolipidosis II, Infantile Free Sialic Acid Storage Disease/ISSD, Juvenile Hexosaminidase A Deficiency, Krabbe disease, Lysosomal acid lipase deficiency, Metachromatic Leukodystrophy, Mucopolysaccharidoses disorders, Multiple sulfatase deficiency, Niemann-Pick Disease, Neuronal Ceroid Lipofuscinoses, Pompe disease/Glycogen storage disease type II, Pycnodysostosis, Sandhoff disease/Adult Onset/GM2 Gangliosidosis, Sandhoff disease/GM2 gangliosidosis—Infantile, Sandhoff disease/GM2 gangliosidosis—Juvenile, Schindler disease, Salla disease/Sialic Acid Storage Disease, Tay-Sachs/GM2 gangliosidosis, Wolman disease, Spinocerebellar ataxia, Autosomal recessive spastic ataxia of Charlevoix-Saguenay, Episodic ataxias (Eas), autosomal recessive cerebellar ataxias (ARCAs), Spinal Muscular atrophy, Parkinson's disease, Taupaties, Progroid syndrome, Werner syndrome, Polyneuropathy, hearing loss, ataxia, retinitis pigmentosa, and cataract (PHARC), Charcot-Marie-Tooth (CMT), Prion diseases, infantile neuronal ceroid lipofuscinosis, familial encephalopathy with neuroserpin inclusion bodies, Darier's disease, Laminopathies, Emery-Dreifuss muscular dystrophy, limb girdle muscular dystrophy type 1B, Dunnigan-type familial partial lipodystrophy, Barraquer-Simons syndrome, Buschke-Ollendorff syndrome, Familial partial lipodystrophy of the Dunnigan type (FPLD), Leukodystrophy, demyelinating, adult-onset, autosomal dominant (ADLD), Pelizaeus-Merzbacher disease, and any combinations thereof.

In some embodiments and aspects of the presently disclosed subject matter the genetic neurodegenerative or neurodevelopmental disease is the Rett syndrome.

The term "Rett syndrome", or "RTT" (originally termed cerebroatrophic hyperammonemia) as herein defined refers to is a neuro-developmental disorder of the grey matter of the brain that almost exclusively affects females (Rett syndrome affects one in every 12,500 female live births by age 12 years). The clinical features include small hands and feet and a deceleration of the rate of head growth (including microcephaly in some). People with Rett syndrome are prone to gastrointestinal disorders, they typically have no verbal skills, and about 50% of individuals affected do not walk. Scoliosis, growth failure, and constipation are very common and can be problematic.

Genetically, Rett syndrome is caused by mutations in the gene MECP2 located on the X chromosome, and can arise sporadically or from germline mutations. Rett syndrome was initially diagnosed by clinical observation, but the diagnosis is definitive when there is a genetic defect in the MECP2 gene. In about 95% of Rett syndrome cases, the cause is a de novo mutation in the child.

At least 200 different mutations of the affected gene methyl-CpG binding protein-2 (MeCP2) have been found to be associated with Rett syndrome, including missense, nonsense (in which premature termination of translated protein occurs), frame shift and deletions.

Therefore in an embodiment of the presently disclosed subject matter, provided is a composition comprising at least one antibiotic macrolide for use in a method of treating Rett syndrome associated with a nonsense mutation in a patient in need thereof, wherein said composition is administered intrathecally in a therapeutically effective dose and wherein said at least one antibiotic macrolide induces read-through of said nonsense mutation and is identified by the method comprising:

a. contacting a candidate antibiotic macrolide with a population of cells containing a nucleic acid construct comprising: (i) an upstream nucleic acid sequence encoding a fluorescent protein selected from GFP and BFP; (ii) a downstream nucleic acid sequence encoding a fluorescent protein different from the upstream fluorescent protein and selected from GFP and BFP; and (iii) a nucleic acid sequence comprising a nonsense mutation associated with Rett syndrome, interposed between the upstream and downstream nucleic acid sequences; wherein the upstream, downstream and interposed nucleic acid sequences are linked in-frame in a single ORF; and b. measuring the fluorescence of the downstream fluorescent protein;

wherein an increase in the fluorescence level of the downstream fluorescent protein in the cells containing said nucleic acid construct contacted with said candidate antibiotic macrolide compared to cells containing said nucleic acid construct and not contacted with said candidate antibiotic macrolide is indicative that the candidate antibiotic macrolide induces read-through of said nonsense mutation.

In other embodiments and aspects of the presently disclosed subject matter the genetic neurodegenerative or neurodevelopmental disease is Ataxia telangiectasia (A-T).

The term "Ataxia telangiectasia" (A-T) (also referred to as Louis-Bar syndrome) as herein defined is a rare, neurodegenerative, inherited disease causing severe disability. Ataxia refers to poor coordination and telangiectasia to small dilated blood vessels, both of which are hallmarks of the disease. A-T impairs certain areas of the brain including the cerebellum, causing difficulty with movement and coordination, weakens the immune system causing a predisposition to infection and prevents repair of broken DNA, increasing the risk of cancer. A-T is caused by a defect in the Ataxia telangiectasia mutated (ATM) gene, which may be, inter alia, a premature termination codon. ATM is a serine/threonine protein kinase that is recruited and activated by DNA double-strand breaks.

Thus in another embodiment of the presently disclosed subject matter, provided is a composition comprising at least one antibiotic macrolide for use in a method of treating Ataxia telangiectasia associated with a nonsense mutation in a patient in need thereof, wherein said composition is administered intrathecally in a therapeutically effective dose and wherein said at least one antibiotic macrolide induces read-through of said nonsense mutation and is identified by the method comprising:
  a. contacting a candidate antibiotic macrolide with a population of cells containing a nucleic acid construct comprising: (i) an upstream nucleic acid sequence encoding a fluorescent protein selected from GFP and BFP; (ii) a downstream nucleic acid sequence encoding a fluorescent protein different from the upstream fluorescent protein and selected from GFP and BFP; and (iii) a nucleic acid sequence comprising a nonsense mutation associated with Ataxia telangiectasia, interposed between the upstream and downstream nucleic acid sequences; wherein the upstream, downstream and interposed nucleic acid sequences are linked in-frame in a single ORF; and
  b. measuring the fluorescence of the downstream fluorescent protein;
wherein an increase in the fluorescence level of the downstream fluorescent protein in the cells containing said nucleic acid construct contacted with said candidate antibiotic macrolide compared to cells containing said nucleic acid construct and not contacted with said candidate antibiotic macrolide is indicative that the candidate antibiotic macrolide induces read-through of said nonsense mutation.

As exemplified below, the effect of different doses of erythromycin was tested on the read-through of two additional nonsense mutations in genes associated with orphan diseases such as for example Usher syndrome, as demonstrated in FIG. 4A and FIG. 4B (example 5).

In other embodiments of the presently disclosed subject matter, provided is a composition comprising at least one antibiotic macrolide for use in a method of treating the Usher syndrome in a patient in need thereof, wherein said composition is administered intrathecally in a therapeutically effective dose.

The term "Usher syndrome" as herein defined refers to a condition characterized by hearing loss or deafness and progressive vision loss. The loss of vision is caused by an eye disease called retinitis pigmentosa (RP), which affects the layer of light-sensitive tissue at the back of the eye (the retina). Vision loss occurs as the light-sensing cells of the retina gradually deteriorate. Night vision loss begins first, followed by blind spots that develop in the side (peripheral) vision. Over time, these blind spots enlarge and merge to produce tunnel vision. In some cases of Usher syndrome, vision is further impaired by clouding of the lens of the eye (cataracts). Three major types of Usher syndrome were identified, designated as types I, II, and III. These types are distinguished by their severity and the age when signs and symptoms appear.

As exemplified in example 9 below, the composition in accordance with the present disclosure was also effective in inducing the translation of the full length SMN2 protein, which is identical to the SMN1 protein as detailed herein below, in fibroblasts obtained from spinal muscular atrophy patients.

Therefore in another one of its aspects of the presently disclosed subject matter provided is a composition comprising at least one antibiotic macrolide for use in a method of treating Spinal Muscular Atrophy (SMA) in a patient in need thereof.

The term "Spinal muscular atrophy" (SMA) as herein defined is an inherited autosomal recessive neurodegenerative disease caused by loss of survival motor neuron 1 (SMN1) gene. SMA is the leading genetic cause of infantile mortality worldwide with a disease prevalence of approximately 1:6000-1:10,000. SMA is characterized by the degeneration of motor neurons within the anterior horn of the spinal cord leading to skeletal muscle weakness and atrophy. Muscle weakness and atrophy is symmetrical and progressive, often impacting the legs more so than the arms, eventually leading to a decline in intercostals activity. Respiratory failure and complications account for the majority of premature deaths in SMA patients (18).

All SMA patients retain one or more copies of SMN2 gene that is nearly identical to the SMN1 gene, differentiated only by a silent, single-nucleotide transition within exon 7. The single nonpolymorphic nucleotide difference at the 5' end of exon 7 (840C>T) of SMN2 renders the majority of SMN2-derived transcripts alternatively spliced, producing an isoform that lacks the typical final coding exon (exon 7). Thus, SMN2 produces low levels of full length SMN and high levels of the truncated SMNΔ7 isoform. The full-length protein produced by SMN2 is identical to the functional, non-defective protein produced by SMN1 (both full length, non-defective or non-trancated proteins SMN1 and SMN2 may be referred to herein as SMN protein). SMA is thus associated also with the premature stop codon in the SMN2 gene.

The truncated SMNΔ7 protein product is dysfunctional and unstable. The small amount of the functional protein that is produced from SMN2 gene is not able to fully compensate for the loss of SMN1. The SMN2 gene comprises a premature stop codon.

Therefore in some embodiments the composition in accordance with the present disclosure is wherein said at least one antibiotic macrolide increases the production of full length SMN2.

By the term "increases the production of full length SMN" it is meant at least a partial increase, increment or rise in the translation of full length SMN. Said increase, increment or rise in the translation of full length SMN may be by at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or about 100%.

In an embodiment of the presently disclosed subject matter, provided is a composition comprising at least one antibiotic macrolide for use in a method of treating Spinal Muscular Atrophy (SMA) in a patient in need thereof, wherein said composition is administered non-systemically.

In another embodiment of the presently disclosed subject matter, provided is a composition comprising at least one antibiotic macrolide for use in a method of treating Spinal Muscular Atrophy (SMA) in a patient in need thereof, wherein said composition is administered non-systemically and wherein said at least one antibiotic macrolide induces read-through of a premature stop codon present in the SMN2 gene, thereby increasing the levels of SMN2 full length protein. In still another embodiment of the presently disclosed subject matter, provided is a composition comprising at least one antibiotic macrolide for use in a method of treating Spinal Muscular Atrophy (SMA) in a patient in need thereof, wherein said composition is administered non-systemically, wherein said at least one antibiotic macrolide induces read-through of a stop codon in the SMN2 gene and wherein said at least one antibiotic macrolide is identified by the method comprising:

a. contacting a candidate antibiotic macrolide with a population of cells containing a nucleic acid construct comprising: (i) an upstream nucleic acid sequence encoding a fluorescent protein selected from GFP and BFP; (ii) a downstream nucleic acid sequence encoding a fluorescent protein different from the upstream fluorescent protein and selected from GFP and BFP; and (iii) a nucleic acid sequence of at least 45 nucleotides corresponding to a fragment of the SMN2 gene comprising the stop codon present in said SMN2 gene, interposed between the upstream and downstream nucleic acid sequences; wherein the upstream, downstream and interposed nucleic acid sequences are linked in-frame in a single ORF; and b. measuring the fluorescence of the downstream fluorescent protein;

wherein an increase in the fluorescence level of the downstream fluorescent protein in the cells containing said nucleic acid construct contacted with said candidate antibiotic macrolide compared to cells containing said nucleic acid construct and not contacted with said candidate antibiotic macrolide is indicative that the candidate antibiotic macrolide induces read-through of said stop codon.

In some embodiments the nucleic acid sequence of at least 45 nucleotides corresponding to a fragment of SMN2 gene (the SMN2 gene is denoted herein by SEQ ID NO. 11) comprising a stop codon present in the SMN2 gene.

In some embodiments the composition comprising at least one antibiotic macrolide for use in a method of treating Spinal Muscular Atrophy (SMA) as herein defined is administered directly to the CNS.

In other embodiments the composition comprising at least one antibiotic macrolide for use in a method of treating Spinal Muscular Atrophy (SMA) as herein defined is administered in a route of administration selected from the group consisting of intrathecal, intraneural, intra-cerebral, intra-ventricular and intra-cranial.

In further embodiments the composition comprising at least one antibiotic macrolide for use in a method of treating Spinal Muscular Atrophy (SMA) as herein defined is administered intrathecally.

In other words, in still another embodiment of the presently disclosed subject matter, provided is a composition comprising at least one antibiotic macrolide for use in a method of treating Spinal Muscular Atrophy (SMA) in a patient in need thereof, wherein said composition is administered intrathecally, wherein said at least one antibiotic macrolide induces read-through of a stop codon present in the SMN2 gene and wherein said at least one antibiotic macrolide is identified by the method comprising:

a. contacting a candidate antibiotic macrolide with a population of cells containing a nucleic acid construct comprising: (i) an upstream nucleic acid sequence encoding a fluorescent protein selected from GFP and BFP; (ii) a downstream nucleic acid sequence encoding a fluorescent protein different from the upstream fluorescent protein and selected from GFP and BFP; and (iii) a nucleic acid sequence of at least 45 nucleotides corresponding to a fragment of the SMN2 gene comprising the stop codon present in said SMN2 gene, interposed between the upstream and downstream nucleic acid sequences; wherein the upstream, downstream and interposed nucleic acid sequences are linked in-frame in a single ORF; and b. measuring the fluorescence of the downstream fluorescent protein;

wherein an increase in the fluorescence level of the downstream fluorescent protein in the cells containing said nucleic acid construct contacted with said candidate antibiotic macrolide compared to cells containing said nucleic acid construct and not contacted with said candidate antibiotic macrolide is indicative that the candidate antibiotic macrolide induces read-through of said stop codon.

In all aspects and embodiments of the presently disclosed subject matter the "composition" as herein defined can also be a "pharmaceutical composition" or a "medical composition".

As used herein, the term "pharmaceutical composition" refers to a preparation of one or more compounds (macrolides) described herein, along with other inert chemical components such as suitable pharmaceutically acceptable carriers. The purpose of a pharmaceutical composition is to facilitate administration of an active ingredient (macrolide antibiotic) to a subject.

Techniques for formulation and administration of drugs may be found, for example, in "Remington's Pharmaceutical Sciences", Mack Publishing Co., Easton, Pa., (Remington: The Science and Practice of Pharmacy, Gennaro, A., Lippincott, Williams & Wilkins, Philadelphia, Pa., 20th ed, 2000). Pharmaceutical compositions of the present invention may be manufactured by processes well known in the art, e.g., by means of conventional mixing, dissolving, granulating, dragee-making, levigating, emulsifying, encapsulating, entrapping, or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations that can be used pharmaceutically. Proper formulation is dependent upon the route of administration chosen.

Examples, without limitation, of carriers are lactose, sucrose, water, organic solvents and polyethyleneglycol.

The carriers may include additional excipients such as binders, disintegrants, lubricants, surface active agents (surfactants), emulsifiers, preservatives and favoring agents.

Pharmaceutical compositions for use in the context of the present invention include compositions wherein the active ingredient is contained in an amount effective to achieve the intended purpose, as further detailed herein below.

The presently disclosed subject matter further provides a method of treating a genetic neurodegenerative or neurodevelopmental disease associated with a nonsense mutation in a patient in need thereof, said method comprising administering a composition comprising at least one antibiotic macrolide.

As used herein the term "treating" or "treatment" of a genetic neurodegenerative or neurodevelopmental disease associated with a nonsense mutation or a symptom or characteristic of such disease may include at least one of the following: (1) preventing the disease, i.e. causing the clinical symptoms or signs of the disease not to develop in a mammal that may be exposed to or predisposed to the disease (e.g., a mammal who expresses a mutated gene) but which does not yet experience or display symptoms or signs of the disease; (2) inhibiting the disease, i.e., arresting or reducing the rate of development of the disease or its clinical symptoms or signs; (3) relieving or alleviating the disease, i.e., causing partial or complete regression of the disease or its clinical symptoms or signs. The term "treating" encompasses promoting formation/production of a functional protein.

Still further the presently disclosed subject matter provides a method of treating Spinal Muscular Atrophy (SMA) in a patient in need thereof, said method comprising administering a composition comprising at least one antibiotic macrolide.

The presently disclosed subject matter further provides a nucleic acid construct comprising:
a. a first nucleic acid sequence encoding a green-fluorescence-protein (GFP);
b. a second nucleic acid sequence encoding a blue-fluorescence-protein (BFP); and
c. a third nucleic acid sequence of at least 45 nucleotides interposed between the first and second nucleic acid sequences, wherein the third nucleic acid sequence comprises a nonsense mutation;
wherein the first, second and third nucleic acid sequences are linked in-frame in a single open reading frame (ORF).

Generally, the structure of the nucleic acid construct of the present disclosure may contain the following in a 5' to 3' direction: (1) a promoter; (2) a polynucleotide encoding a first fluorescent protein; (3) a sequence of at least 45 nucleotides comprising a nonsense mutation (also termed herein a "premature stop codon"); (4) a polynucleotide encoding a second fluorescent protein; and (6) a normal termination signal.

The constructs as herein defined thus comprise a sequence of at least 45 nucleotides comprising a nonsense mutation, namely a mutated sequence which corresponds to or is homologous to a mutated sequence in a gene associated with a known genetic neurodegenerative or neurodevelopmental disease, where the "mutation" is a premature termination or stop codon.

The premature termination codon may be any known stop codon (UAG, UAA and UGA). Typically, the length of the sequence containing the mutation or the premature stop codon is at least 45 nucleotides, for example at least 46, at least 47, at least 48, at least 49, at least 50 nucleotides. The mutation or premature stop codon is usually in the middle of the sequence.

As used herein, the term "nucleic acid" or "polynucleotide(s)", means a single or double-stranded deoxyribonucleotide or ribonucleotide polymer.

The term "construct", as used herein refers to an artificially assembled or isolated nucleic acid molecule which may be comprised of one or more nucleic acid sequences, wherein the nucleic acid sequences may be coding sequences (that is, sequence which encodes for an end product), regulatory sequences, non-coding sequences, or any combination thereof.

As referred to herein, the term, "Open Reading Frame" ("ORF") is directed to a coding region which contains one start codon and one stop codon. It is to be understood that an open reading frame according to the present invention may include a mutated, premature stop codon located between the "normal" start and stop codons noted above. If read-through does not occur, the resulting protein will end at the premature termination codon. In case read-through does occur, the entire ORF will be translated in full.

As used herein, the term "in frame", when referring to one or more nucleic acid sequences, indicates that these sequences are linked such that their correct reading frame is preserved.

By the term "linked" as herein defined it is meant that the various nucleic acid sequences are covalently bonded, in phosphodiester bond.

By the term "interposed between" it is meant that a nucleic acid sequence or oligonucleotide, for example a nucleic acid sequence of at least 45 nucleotides, is flanked at both ends (upstream and downstream) by other nucleic acid sequences, specifically nucleic acid sequences encoding fluorescent proteins. Specific interposed nucleic acid sequences of at least 45 nucleotides are those homologous or corresponding to a fragment of a mutated protein which harbors a nonsense mutation or stop codon, as described herein.

The terms "Upstream" and "Downstream", as used herein refers to a relative position in a nucleotide sequence, such as, for example, a DNA sequence or an RNA sequence. As well known, a nucleotide sequence has a 5' end and a 3' end, so called for the carbons on the sugar (deoxyribose or ribose) ring of the nucleotide backbone. Hence, relative to the position on the nucleotide sequence, the term downstream relates to the region towards the 3' end of the sequence. The term upstream relates to the region towards the 5' end of the strand.

The constructs utilized herein includes green and blue fluorescent proteins.

Suitable blue fluorescent proteins include: EBFP (380-440), EBFP2 (383-448) from Addgene and TagBFP (402-457) from Evrogene. Suitable green fluorescent proteins include: EGFP (488-507) from Addgene, TurboGFP (482-502), TagGFP (482-505), ACGFP1 (484-510), TagGFP2 (483-506) from Evrogene and Emerald (487-509) from Invitrogene. The numbers refer to Excitation (nm) and Emission (nm) of each fluorescent protein to be chosen according to the specific FACS machine lasers and filters. The sequences of the above proteins and sequences encoding them are known in the art.

In specific embodiments the GFP as used herein is having the nucleic acid sequence as denoted by SEQ ID NO. 9 and the BFP as used herein is having the nucleic acid sequence as denoted by SEQ ID NO. 10.

In some embodiments the nucleic acid construct as herein defined is wherein GFP is upstream to BFP.

As exemplified above, the inventors have utilized a nucleic acid construct comprising a first nucleic acid sequence encoding GFP, a second nucleic acid sequence encoding BFP and a third nucleic acid sequence of at least 45 nucleotides interposed between the GFP and the BFP, where the third nucleic acid sequence comprised a nonsense mutation.

In some embodiments the third nucleic acid sequence comprises the nonsense mutation (stop codon) carried in the gene encoding the ataxia telangiectasia mutated (ATM) protein, where the nucleic acid sequence comprising the stop codon is denoted by SEQ ID NO. 3. Such a nucleic acid construct may be used for identifying an agent (e.g. a macrolide or an antibiotic macrolide) that induces read-through of a nonsense mutation associated with ataxia telangiectasia, where the agent identified may be used for the treatment of this disease.

In other embodiments the third nucleic acid sequence comprises a nonsense mutation (stop codon) carried in the gene cadherin-23 gene (CDH23), where the nucleic acid sequence comprising the stop codon is denoted by SEQ ID NO. 6. Such a nucleic acid construct may be used for identifying an agent (e.g. a macrolide or an antibiotic macrolide) that induces read-through of a nonsense mutation associated with the Usher syndrome, where the agent identified may be used for the treatment of this disease.

In other embodiments the third nucleic acid sequence comprises the nonsense mutation (stop codon) carried in the MECP2 gene, where the nucleic acid sequence comprising the stop codon is denoted by SEQ ID NO. 8. Such a nucleic acid construct may be used for identifying an agent (e.g. a macrolide or an antibiotic macrolide) that induces read-through of a nonsense mutation associated with the Rett syndrome, where the agent identified may be used for the treatment of this disease.

In other embodiments the third nucleic acid sequence comprises a stop codon naturally carried in the SMN2 gene encoding the SMN2 protein (the SMN2 gene being denoted by SEQ ID NO. 11). Such a nucleic acid construct may be used for identifying an agent (e.g. a macrolide or an antibiotic macrolide) that induces read-through of a nonsense mutation associated with spinal muscular atrophy (SMA), where the agent identified may be used for the treatment of this disease.

In some embodiments, the construct of the present invention comprises one or more linker sequences interposed between the first, second and third sequences. Such linker sequences may be inserted, for example, to maintain the open reading frame.

In other embodiments the nucleic acid construct as herein defined further comprises one or more linker nucleic acid sequences interposed between the first, second and third nucleic acid sequences.

Any type of plasmid, cosmid, YAC or viral vector can be used to prepare a recombinant DNA constructs comprising the nucleic acid construct as herein defined which can be introduced directly into a target cell/cell population. Alternatively, viral vectors can be used which selectively infect the desired target cell.

In some embodiment the presently disclosed subject matter provides a vector comprising the nucleic acid construct as herein defined.

The term "vector" refers to a polynucleotide molecule, usually double stranded DNA, which is used to transport a construct into a host cell, and/or express a nucleic acid sequence contained within the construct in the host cell. The vector may be capable of replication in at least one additional host system, such as *E. coli*. The vector may also include a sequence to allow for selection of cells containing the vector. Many viral, prokaryotic and eukaryotic expression vectors are known and/or commercially available. Selection of appropriate expression vectors is within the knowledge of those having skill in the art.

The viral vector may be selected from, but is not limited to: Herpesviridae, Poxyiridae, Adenoviridae, Adeno-associated virus, Papillomaviridae, Parvoviridae, Hepadnoviridae, Retroviridae, Reoviridae, Filoviridae, Paramyxoviridae, Pneumoviridae, Rhabdoviridae, Orthomyxoviridae, Bunyaviridae, Hantaviridae, Picornaviridae, Caliciviridae, Togaviridae, Flaviviridae, Arenaviridae, Coronaviridae, or Hepaciviridae.

As known in the art, the vector may further comprise various other polynucleotide sequences that are required for its operation (such as, for example, regulatory sequences, non coding sequences, structural sequences, and the like).

In some embodiments, the methods comprise transfecting a host cells with the nucleic acid construct. The transfected cells are then contacted with a tested agent.

Thus the presently disclosed subject matter provides a host cell comprising the nucleic acid construct as herein defined or a host cell transfected with the vector as herein defined, which comprises the nucleic acid construct of the presently disclosed subject matter.

Any cell or cell line of any species well-known to one of skill in the art may be utilized in accordance with the methods of the invention.

In some embodiments the host cell of the present disclosure is a eukaryotic cell.

In other embodiments the host cell of the present disclosure is a mammalian cell.

The nucleic acid molecules can be prepared by any method known in the art for the synthesis of nucleic acid molecules. For example, they may be chemically synthesized using commercially available reagents and synthesizers by methods that are well known in the art.

Methods for producing assembling constructs and vectors are well known in the art and are described generally in Sambrook et ah, Molecular Cloning: A Laboratory Manual, 2nd Ed. Cold Spring Harbor Press, 1987; Ausubel et ah, Current Protocols in Molecular Biology, Greene Publishing, 1987).

The terms "promoter element", "Promoter" or "promoter sequence" as used herein, refer to a nucleotide sequence that is generally located at the 5' end (that is, precedes, located upstream) of the coding sequence and functions as a switch, activating the expression of a coding sequence. If the coding sequence is activated, it is said to be transcribed. Transcription generally involves the synthesis of an RNA molecule (such as, for example, a mRNA) from a coding sequence. The promoter, therefore, serves as a transcriptional regulatory element and also provides a site for initiation of transcription of the coding sequence into mRNA. Promoters may be derived in their entirety from a native source, or be composed of different elements derived from different promoters found in nature, or even comprise synthetic nucleotide segments.

It is understood by those skilled in the art that different promoters may direct the expression of a gene in different tissues or cell types, or at different stages of development, or in response to different environmental conditions, or at various expression levels. Promoters which cause a gene to be expressed in most cell types at most times are commonly referred to as "constitutive promoters". Promoters that derive gene expression in a specific tissue are called "tissue specific promoters".

Exemplary promoters that may be used include, but are not limited to: the SV40 early promoter region, Thymidine Kinase, the promoter contained in the 3' long terminal repeat of Rous sarcoma virus, the herpes thymidine kinase promoter, the regulatory sequences of the metallothionein gene, the viral CMV promoter, the human chorionic gonadotropin-beta promoter, etc.

As used herein, the terms "introducing" and "transfection" or "transfecting" may interchangeably be used and refer to the transfer of molecules, such as, for example, nucleic acids, polynucleotide molecules, vectors, and the like into a target cell(s), and more specifically into the interior of a membrane-enclosed space of a target cell(s). The molecules can be "introduced" into the target cell(s) by any means known to those of skill in the art, for example as taught by Sambrook et al. Molecular Cloning: A Laboratory Manual, Cold Spring Harbor Laboratory Press, New York (2001). Means of "introducing" molecules into a cell include, for example, but are not limited to: heat shock, calcium phosphate transfection, PEI transfection, electroporation, lipofection, transfection reagent(s), viral-mediated transfer, and the like, or combinations thereof. The transfection of the cell may be performed on any type of cell, of any origin, such as, for example, human cells, animal cells, plant cells, and the like.

The host cells of the invention, or for use in the screening methods of the invention, may be any type of cell. In some embodiments, the host cells are eukaryotic. In some embodiments, the host cells are mammalian cells. Exemplary mammalian cell type includes HEK293T and HCT116.

Host cells may be transiently transformed with constructs or vectors. Alternatively host cell lines may be developed which are stably transformed with a construct of the invention. Methods for transient or stable transformation are well-known to those skilled in the art.

According to an aspect of the present invention, methods for identifying agents that are capable of inducing read-through of premature termination codons are provided.

The presently disclose subject matter further provides a method for identifying an agent that induces read-through of a nonsense mutation, as detailed below. The candidate agent that induces read-through may be, inter alia, a macrolide or antibiotic macrolide.

Thus by a further aspect of the presently disclosed subject matter provided is a method for identifying a macrolide that induces read-through of a nonsense mutation, the method comprising:
a. contacting a candidate macrolide with a population of cells containing a nucleic acid construct comprising: (i) an upstream nucleic acid sequence encoding a fluorescent protein selected from GFP and BFP; (ii) a downstream nucleic acid sequence encoding a fluorescent protein different from the upstream fluorescent protein and selected from GFP and BFP; and (iii) a nucleic acid sequence comprising a nonsense mutation associated with a genetic neurodegenerative or neurodevelopmental disease, interposed between the upstream and downstream nucleic acid sequences; wherein the upstream, downstream and interposed nucleic acid sequences are linked in-frame in a single ORF; and
b. measuring the fluorescence of the downstream fluorescent protein;
wherein an increase in the fluorescence level of the downstream fluorescent protein in the cells containing said nucleic acid construct contacted with said candidate macrolide compared to cells containing said nucleic acid construct and not contacted with said candidate macrolide is indicative that the candidate macrolide induces read-through of a nonsense mutation.

The methods comprise contacting cells containing the nucleic acid construct of the present invention with a tested agent. The nucleic acid construct comprises a sequence encoding a first, upstream fluorescent protein, and a sequence encoding a second, downstream fluorescent protein. These two sequences are separated by a sequence comprising a nonsense mutation. Preferably, this sequence is of at least 45 nucleotides.

It is understood that the "contacting" is performed under conditions that allows transcription and translation (expression) of the nucleic acid sequences contained within the construct. For example, if the construct contains an inducible promoter, a suitable inducing molecule should be added to the test sample. In addition, contacting is preferably conducted in an aqueous solution comprising a buffer and a combination of salts (such as KCl, NaCl and or MgCl2).

The methods of the present invention can be performed using different incubation times. The incubation times may be at least 12 hours, at least 18 hours, at least 24 hours, at least 36 hours, at least 48 hours before the fluorescence is measured.

The methods further comprise measuring the fluorescence of the downstream fluorescent protein in cells expressing the construct in the presence of the agent and in cells expressing the construct in the absence of the agent. An increase in the fluorescence level of the downstream fluorescent protein in the cells contacted with the agent (e.g. a macrolide or an antibiotic macrolide) compared to cells not contacted with the agent is indicative of the agent being a read-through agent (e.g. a macrolide or an antibiotic macrolide). In some embodiments, an increase of at least about 2-15% is indicative that the agent is a suitable read-through agent for clinical applications.

Measuring the fluorescence of the downstream fluorescent protein may be performed by a fluorescence-activated cell sorter (FACS). In currently preferred embodiments, cells expressing both the upstream and downstream fluorescent proteins are sorted by the FACS, and the fluorescence intensity of the downstream fluorescent protein is measured only in the sorted cells.

Typically, mean fluorescent intensity (MFI) is calculated for the cell population that was exposed to the agent and for the cell population not exposed to the agent, and the MFI values are compared.

In some embodiments, the methods additionally include the use of a control construct similar to the construct of the invention except that in the control construct there is no nonsense mutation (namely the control construct do not include a premature termination codon), such that the two fluorescent proteins are always co-expressed as a fusion protein, without the need for read-through.

Although the screening methods of the present invention are preferably performed using intact cells for expressing the constructs, and flow cytometry for detection, the methods may be modified to be conducted using in vitro translation, and/or to utilize other techniques for detecting and measuring fluorescence.

In some embodiments, the screening methods are conducted by contacting a candidate readthrough agent with a cell-free extract. Any technique well-known to one of skill in the art may be used to generate cell-free extracts for translation. For example, cell-free extracts can be generated by centrifuging cells and clarifying the supernatant. The cells may be incubated on ice during the preparation of the cell-free extract, for example, for at least 12 hours, at least 24 hours, at least two days, at least five days, at least one week. Preferably, the cells are incubated on ice at least long enough so as to improve the translation activity of the cell extract in comparison to cell extracts that are not incubated on ice. Alternatively, the cells may be incubated at a temperature between about 0° C. and 10° C., for example at about 4° C.

Centrifugation may be performed at a low speed to isolate the cell-free extract for in vitro translation reactions. For example, the cell extract may be the supernatant from cells that are centrifuged at about 2×g to 20,000×g, at about 5×g to 15,000×g, at about 10,000×g. Alternatively, the cell-free extract may be the about SI to S50 extract, for example about the S5 to S25 extract, about the S10 extract.

The cell-free translation extract may be isolated from cells of any species origin. For example, the cell-free translation extract may be isolated from yeast, cultured mouse or rat cells, Chinese hamster ovary (CHO) cells, Xenopus oocytes, reticulocytes, wheat germ, or rye embryo (see, e.g., Krieg & Melton, 1984, Nature 308:203 and Dignam et al, 1990 Methods Enzymol. 182:194-203). Alternatively, the cell-free translation extract, e.g., rabbit reticulocyte lysates and wheat germ extract, can be purchased from, e.g., Promega, (Madison, Wis.). As another alternative, the cell-free translation extract is prepared as described in international Patent Publication No. WO 01/44516 and U.S. Pat. No. 4,668,625. In some embodiments, the cell-free extract is an extract isolated from human cells, for example, HeLa cells.

In some embodiments, the tested agents are screened in pools. Once a positive pool has been identified, the individual compounds of that pool may be tested separately.

In some embodiments the method for identifying a macrolide that induces read-through is wherein the upstream fluorescent protein is GFP and the downstream fluorescent protein is BFP, for example as exemplified herein below.

In other embodiments the method for identifying a macrolide that induces read-through is wherein the interposed nucleic acid sequence comprising a nonsense mutation is of at least 45 nucleotides.

In further embodiments the method for identifying a macrolide that induces read-through is wherein the fluorescence of the downstream fluorescent protein is measured only in cells expressing both the upstream and downstream fluorescent proteins.

In still further embodiments the method for identifying a macrolide that induces read-through comprises detecting or sorting cells expressing both the upstream and downstream fluorescent proteins.

In still further embodiments the method for identifying a macrolide that induces read-through is wherein an increase in the fluorescence level of the downstream fluorescent protein in the cells containing said nucleic acid construct contacted with said candidate macrolide compared to cells containing said nucleic acid construct and not contacted with said candidate macrolide of at least about 7-25% is indicative that the candidate macrolide is a suitable read-through agent for clinical applications.

In some embodiments the method for identifying a macrolide that induces read-through is wherein measuring the fluorescence of the downstream fluorescent protein is performed by a fluorescence-activated cell sorter (FACS).

In some embodiments the method for identifying a macrolide that induces read-through further comprises comparing the fluorescent level of the downstream fluorescent protein between cells containing the construct and contacted with the candidate macrolide to cells containing a control construct with no nonsense mutation.

In other embodiments the method for identifying a macrolide that induces read-through is wherein said macrolide is an antibiotic macrolide.

In yet another aspect of the presently disclosed subject matter provided is a method of treating a genetic neurodegenerative or neurodevelopmental disease resulting from or associated with a nonsense mutation comprising:
(i) selecting a nonsense mutation read-through macrolide for treating a subject in need thereof by a method comprising:
  a. identifying in a biological sample obtained from said subject at least one nonsense mutation in a gene associated with a genetic neurodegenerative or neurodevelopmental disease;
  b. providing a nucleic acid construct comprising a fragment of at least 45 nucleotides corresponding to said identified mutation of (a) and its surrounding nucleotides, flanked by two nucleic acid sequences encoding two distinct fluorescent proteins selected from GFP and BFP, wherein the fragment and the nucleic acid sequences encoding the two distinct fluorescent proteins are linked in-frame in a single ORF;
  c. introducing the construct of (b) into a host cell; and
  d. contacting the host cells containing the construct of (b) with a candidate read-through macrolide; and
  e. detecting the presence of read-through polypeptides containing both fluorescent proteins;
  f. wherein the presence of read-through polypeptides containing both fluorescent proteins is indicative that said candidate read-through macrolide is a nonsense mutation read-through macrolide; and
(ii) administering said nonsense mutation read-through macrolide to said subject.

In some embodiments, the subject to be treated undergoes genetic testing to identify the exact mutation(s) the subject is bearing in a gene associated with a particular disease, in order to verify that the subject would be amenable to treatment with the compositions of the present invention. Genetic tests to identify a specific mutation in a specific gene are known in the art. Such tests are often used in the diagnosis of the genetic diseases described herein.

Information about specific diseases and their associated mutations is available in the scientific literature. Such information may also be found in databases, including for example:
HGMD® Human Gene Mutation Database, available at: www.biobase-international.com/product/hgmd or at: www.hgmd.org/.
OrphaNet: European reference portal for information on rare diseases and orphan drugs, available at: www.orpha.net/consor/cgi-bin/index.php.
OMIM, Online Mendelian Inheritance in Man, available at:
www.ncbi.nlm.nih.gov/omim.

In the above and other embodiments the macrolide as herein defined may be an antibiotic macrolide.

The active agent may be co-administered with another active agent or in combination with another treatment method. In some embodiments, a combination of macrolides is administered.

The term "biological sample" is used in its broadest sense. It is meant to include a specimen or culture obtained from any source, including animals (and humans) and encompass fluids (e.g. blood and lymph), solids and tissues.

Thus by still another one of its aspects the presently disclosed subject matter provides a composition comprising at least one antibiotic macrolide in combination with at least one additional therapeutically effective agent, for use in a method of treating a genetic neurodegenerative or neurodevelopmental disease associated with a nonsense mutation in a patient in need thereof.

Said at least one additional therapeutically effective agent is an agent capable of treating a genetic neurodegenerative or neurodevelopmental disease associated with a nonsense mutation any one of antibacterial agents, and/or of enhancing the therapeutic effect of said macrolide antibiotic. The said at least one additional therapeutically effective agent is administered at suitable dose, which can be a suboptimal dose or a therapeutic dose. The said macrolide antibiotic agent and said at least one additional therapeutically effective agent can be administered simultaneously. Alternatively and additionally, said macrolide antibiotic agent and said at least one additional therapeutically effective agent can be administered at different time points, at different intervals between administrations, for different durations of time, in a different order and/or by a different route of administration.

In some embodiments the "at least one additional therapeutic agent" or "at least one additional therapeutically effective agent" as herein defined may be any therapeutic agent known to be effective for the treatment of a genetic neurodegenerative or neurodevelopmental disease. For example, the at least one additional therapeutic agent may be, but is not limited to, Histone deacetylase inhibitors (HDACi) that promote SMN2 transcription enhancement by repressing DNA chromatin compression, RG3039, which is a scavenger mRNA-decapping enzyme, exon skipping agents, RNA-based therapeutic agents, splice-modulating agents and the like, to name but few.

The compositions and methods of the present invention utilize therapeutically effective amounts of macrolide compounds that are capable of suppressing premature stop codons, or induce readthrough of the premature stop codons.

As used herein, the term "suppression" or "suppressing", when used in reference to premature stop mutations or premature stop codons, means the process of read-through of a stop codon.

The term "therapeutically effective amount" as herein defined includes the amount of the macrolide or antibiotic macrolide of the invention sufficient to induce read-through of the premature stop codons.

The "therapeutically effective amount" may vary depending on the compound, the disease and its status or severity, the age, weight, other medical conditions, etc., of the mammal to be treated. The therapeutically effective amount may also vary depending on one or more past or concurrent medical, surgical, or radiation therapy interventions. The therapeutically effective amount may also vary depending on the type of the stop codon.

Determination of a therapeutically effective amount for the purposes of the present invention is within the capabilities of a person skilled in the art in the field of the invention.

In some embodiment the term "therapeutically effective amount" as used and defined herein is to be taken to mean an amount of the active agent (antibiotic macrolide) that is effective in inducing read-through when administered non-systemically, for example, directly to the CNS or intrathecally, while its systemic levels are sub-microbicidal levels. The therapeutically effective amount administered non-systemically can be 10-, 50-, 100-, 200-, 300-, 350-, 400-, 450-, 500-, 550-, 600-, 650-700-, 750-, 800-, or 900-fold the conventional microbicidal/antibiotic doses administered systemically, and even higher. The terms "microbicidal" "antibiotic" are used herein synonymously and interchanging.

For example, as indicated herein below, administration of azythromycin can be at a dose of 1.5-15 mg per injection, leading to levels of 10-100 µg/ml CSF fluid.

The term "patient in need thereof" as herein defined refers to a subject suffering from a genetic neurodegenerative or neurodevelopmental disease as herein defined.

In some embodiments, the patient in need thereof is a mammal, preferably human.

Further provided are kits, comprising the nucleic acids, the vectors or the host cells of the present invention. Such kits may be used to practice the methods of the present invention. Such kits may include control constructs in addition to the nucleic acids of the present invention. Such kits may include equipment for practicing the disclosed methods, such as tubes, plates, pipettes and the like.

In all aspects and embodiments of the disclosed subject matter, the antibiotic macrolide or composition comprising the same can also be comprised in suitable delivery devices, specifically drug-device combinations. An example of a delivery drug-device combination is an osmotic pump. Delivery drug-device combinations can be coated implantable medical devices, so that a therapeutically effective dose of the antibiotic macrolide or a composition comprising the same is continuously delivered to the patient. The drug-device combination can also be designed for periodically releasing the active agent. By such drug-device combinations, the antibiotic macrolide or a composition comprising the same can be delivered by an osmotic process at a controlled rate. Such systems may be constructed by coating an osmotically active agent with a rate controlling semipermeable membrane. This membrane may contain an orifice of critical size through which agent is delivered. The active agent antibiotic macrolide, after coming into contact with aqueous fluids, imbibes water at a rate determined by the fluid permeability of the membrane and osmotic pressure of the core formulation. This results in formation of a saturated solution of active agent to be dispensed at controlled rate from the delivery orifice in the membrane. The osmotic pump can be implantable, to be implanted at a suitable target site, for example in the CSN of the patient.

As used herein, the term "about", when referring to a measurable value such as an amount, a temporal duration, and the like, is meant to encompass variations of $.+-0.10\%$, more preferably $.+-0.5\%$, even more preferably $.+-0.1\%$, and still more preferably $.+-0.01\%$ from the specified value, as such variations are appropriate to perform the disclosed methods.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Experimental Procedures

Plasmid Construction

The blue fluorescent protein (BFP) was amplified from the pEBFP2-C1 plasmid using the primers KpnI forward, having the nucleic acid sequence of AGA GG TAC CGA GTG AGC AAG GGC GAG GAG (denoted herein as SEQ ID NO. 1) and BamHI reverse, having the nucleic acid AGA GGA TCC GAT CCG GTG GAT CCC GGG CCC (denoted herein as SEQ ID NO. 2).

The PCR product was ligated into pEGFP-C2 plasmid using KpnI and BamHI restriction enzymes to create a GFP-C2-BFP vector. Next, oligonucleotides coding for a desired gene for testing (both wild type and mutated sequences) were inserted into the GFP-C2-BFP digested with XhoI and HindIII, keeping the open reading frame. The plasmid GFP-C2-BFP is schematically presented in FIG. 1A. In particular, FIG. 1C-1 schematically presents the plasmid GFP-C2-BFP with the wild type sequence inserted between the GFP and BFP and FIG. 1C-2 schematically presents the plasmid GFP-C2-BFP with the mutated sequence, containing a stop codon inserted between GFP and BFP.

The Read-Through Assay

HEK293T cells plated on 6 wells were transfected with 2 μg plasmids using the Polyethyleneimine "MAX" transfection reagent (Polysciences Inc.), according to the manufacturer protocol. For each experiment, the GFP-C2-BFP vector containing a fragment of the gene associated with a specific disease (either as the wild type sequence or as the mutated sequence) was used.

Twenty four hours post transfection, the transfected cells were subjected to a treatment with the antibiotic macrolide. The cells were treated with different concentrations of the antibiotic macrolide erythromycin (Sigma), for different periods of time, as detailed below. After the treatment the cells were scraped gently from the wells, washed with PBS (Sigma), and re-suspended in PBS for FACS analysis. FACS analysis was performed using Kaluza® Flow Analysis Software—Beckman Coulter according to manufacturer's instructions. Some of the cells were pelleted, lysed and subjected to polyacrylamide gel electrophoresis (PAGE).

Example 1

Plasmid Constructs and their Preliminary Evaluation

The basic features of the plasmid constructs based on GFP-C2-BFP prepared as described above are presented in FIG. 1A. As shown in FIG. 1A, "WT" indicates wild type sequences and "mut" refers to mutated sequences (that include the nonsense mutations also referred to herein as premature stop codons). As detailed above, these constructs were transfected into mammalian cells (i.e. HEK293T) and treated with different macrolide concentrations for various periods of time. FIG. 1B shows exemplary immunofluorescence photographs of cells transfected with the GFP-C2-BFP constructs.

As schematically presented in FIG. 1C-1, when the plasmid construct was carrying a "wild type" (wt) nucleic acid sequence, namely, where no stop codon was present in the nucleic acid sequence flanked by the green fluorescent protein (GFP) and the blue fluorescent protein (BFP), an in-frame fusion protein comprising GFP and BFP was translated in cells transfected with the plasmid construct. The fluorescence levels of the GFP and BFP were then determined using a Fluorescence-activated cell sorting flow cytometer (FACS).

However, as demonstrated in FIG. 1C-2, when the plasmid construct comprised a mutated nucleic acid sequence ("mut"), namely, a stop codon was present in the nucleic acid sequence flanked by GFP and BFP (also referred to herein as a "nonsense" mutation), only a portion of the construct that comprised GFP was translated in cells transfected with the plasmid construct.

An exemplary FACS analysis of cells transfected with the above constructs is presented in the lower panels of FIG. 1C-1 and FIG. 1C-2, corresponding to the above detailed constructs. As demonstrated in the lower panel of FIG. 1C-3, when cells transfected with the plasmid construct comprising the mutated nucleic acid sequence were incubated in the presence of a macrolide (for example the macrolide Erythromycin), translation of the fusion protein comprising both GFP and BFP was restored. As demonstrated in FIG. 1C-3, lower panel, fluorescence is somewhat shifted compared to the fluorescence shown in the middle lower panel, as a result of the read-through enabled in the presence of the antibiotic macrolide erythromycin.

Figure 1D:
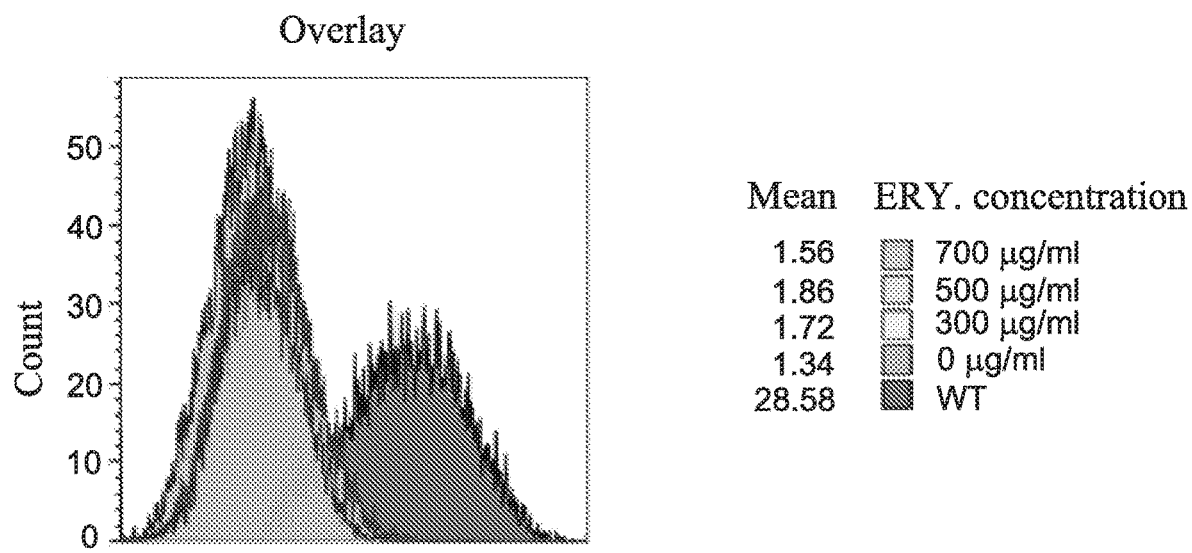
Figure 2:
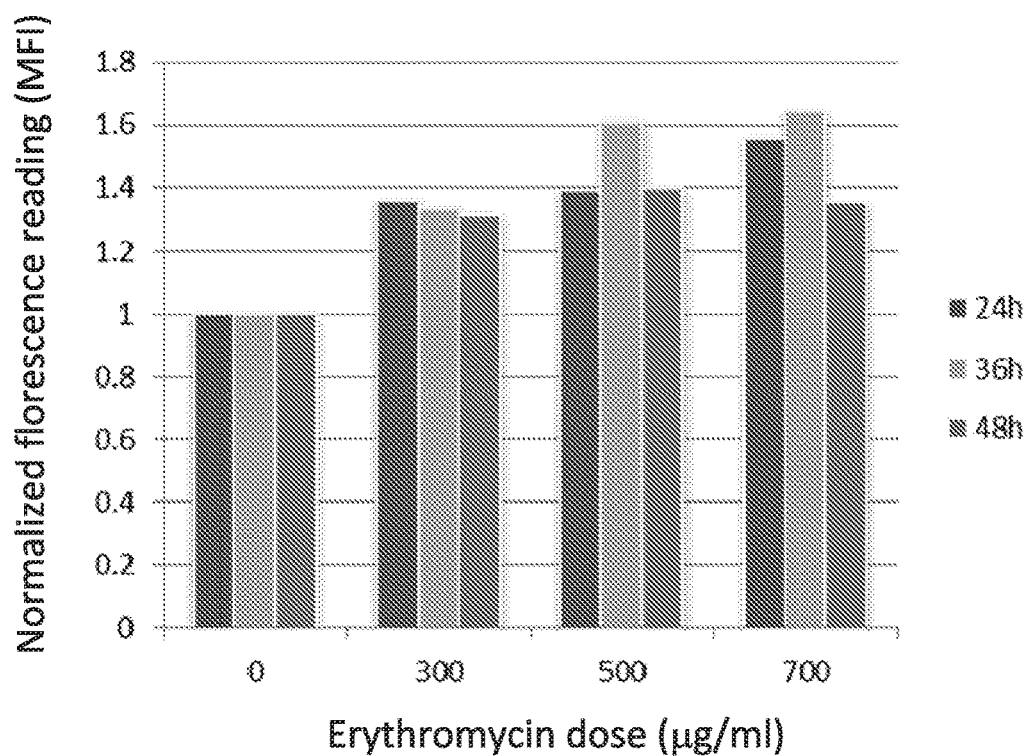

An overlay illustration of the FACS data obtained for cells transfected with a plasmid construct carrying a nonsense mutation and incubated for 24 hours in the presence of different concentrations of erythromycin (0, 300, 500 and 700 μg/ml) is shown in FIG. 1D. The shift in mean values represents the degree of read-through.

Example 2

Assaying the Read-Through of a Plasmid Construct Comprising Ataxia Telangiectasia Mutated (ATM) Sequence Using Macrolides As described in the following sections, erythromycin was able to induce read-through of the premature stop codon found in the gene encoding the Ataxia telangiectasia mutated (ATM) protein.

The ability of erythromycin to induce read-through of the premature stop codon in the gene encoding the ATM protein was assayed by constructing a mutated and a wild type plasmid constructs based on GFP-C2-BFP, as detailed above, in which the following sequences were inserted between the GFP and BFP, respectively: the ATM mutated nucleic acid sequence: aaa ttt aag cgc ctg att Tga gat cct gaa aca att aaa cat, denoted by SEQ ID NO. 3 (the mutated nucleotide is marked in boldface) and the ATM wild type nucleic acid sequence: aaa ttt aag cgc ctg att Cga gat cct gaa aca att aaa cat, denoted by SEQ ID NO. 4. The sequences further included restriction enzyme recognition sequences (not shown).

The plasmids were constructed and transfected to HEK293T cells as described above. Cells transfected with an ATM mutated gene were treated with 300, 500 or 700 μg/ml erythromycin for 24, 36 or 48 hours, or left untreated ("0" erythromycin). For each group, the median fluorescence intensity (MFI) of BFP was calculated. BFP reading were only collected from GFP expressing cells.

The effect of different erythromycin doses and various incubations durations on the read-through of the premature stop codon in the gene encoding the ATM protein (the ATM mutation) is presented in FIG. 2, which demonstrates that erythromycin is able to induce read-through of the premature stop codon found in the gene encoding the ATM protein.

The WT results were omitted as they are extremely high and irrelevant for the analysis. The median value of each reading of the different doses were normalized and are presented relative to no treatment results ("0" erythromycin).

Example 3

ATM Protein Restoration Using Macrolides

In this experiment, B-lymphocytes obtained from Ataxia telangiectasia (A-T) patients carrying a heterozygous nonsense mutation C5515→T (Coriell, #GM11264), in comparison to WT cells, were incubated for 7 days in the presence of the antibiotic macrolides Gentamycin, Erythromycin or Azithromycin at either 300 μg/ml concentration (as shown in FIG. 3A) or lower (100 μg/ml for Erythromycin, as shown in FIG. 3B). Cells were then harvested and subjected to SDS-PAGE and Western analysis using specific anti-ATM antibodies. Band intensities were analyzed for the results shown in FIG. 3B using the TINA software and are shown in FIG. 3C.

FIG. 3D shows homozygous A-T mutant C103→T and WT cells (both are the generous gift of Prof. Yosi Shilo, Tel Aviv University, Israel) that were incubated n the presence of Erythromycin (E), either at 100 or 300 µg/ml for 7 days. Cells were then harvested and subjected to SDS-PAGE analysis using specific anti-ATM antibodies.

Example 4

Validation of Restoration of a Functional ATM Protein Using Macrolides

The expression of the ATM protein is also assayed in a functional assay, in suitable mammalian cells, using a plasmid that encodes the ATM protein (mutated or wild type) tagged at its C'-terminus with a FLAG epitope.

Mutated ATM protein is obtained using site-directed mutagenesis (STRATAGENE), thereby disease-causing nonsense mutations are inserted in the ATM gene at known sites. Following treatment with stop-codon read-through agents, and optionally a promoter activating and (NMD) compound, cells transfected with these plasmids are examined for activities of the ATM gene, for example radioresistance. Additional functionality tests are also done.

Example 5

Usher Syndrome and Rett Syndrome

The following experiments were performed in order to test the effect of different doses of erythromycin on the read-through of additional three nonsense mutations in genes associated with the orphan diseases Usher syndrome and Rett syndrome. All these diseases are caused, at least partially, by nonsense mutations.

For these experiments, GFP-C2-BFP plasmids comprising the following sequences inserted between the GFP and BFP were prepared, as described above. Briefly, the plasmids were constructed as follows:

(1) A plasmid comprising the wild type sequence of a fragment of the cadherin-23 gene (CDH23) associated with the Usher syndrome, comprised the nucleic acid sequence: tat ctc tat gat gtg ctg cga atg tac cac cag acc atg gac, as denoted by SEQ ID NO. 5;

(2) A plasmid comprising a mutated sequence of the above fragment of the cadherin-23 gene, comprised the nucleic acid sequence: tat ctc tat gat gtg ctg Tga atg tac cac cag acc atg gac, as denoted by SEQ ID NO. 6;

(3) A plasmid comprising the wild type sequence of a fragment of the MECP2 gene associated with the Rett syndrome, comprised the nucleic acid sequence: aga ggg agc ccc tcc cgg cga gag cag aaa cca cct aag aag, as denoted by SEQ ID NO. 7;

(4) A plasmid comprising a mutated sequence of the above fragment of the MECP2 gene, comprised the nucleic acid sequence: aga ggg agc ccc tcc cgg Tga gag cag aaa cca cct aag aag, as denoted by SEQ ID NO. 8.

As described above, the plasmids further included restriction enzyme recognition sequences (not shown).

In addition, the GFP-C2-BFP plasmid comprising the nucleic acid insert which comprises the nonsense mutation associated with ATM, as described above, was also tested in this experiment. The plasmids were constructed and transfected to cells as described above. Cells transfected with a plasmid comprising a mutated gene fragment were treated with 300, 500 or 700 µg/ml erythromycin for 24 or 48 hours, or left untreated ("0" erythromycin). For each group, the median fluorescence intensity (MFI) of BFP was monitored using FACS analysis and calculated. The effect of erythromycin on read-through of the nonsense mutated sequences corresponding to the four disorders is presented in FIG. 4 (FIG. 4A relates to 24 hours incubation and FIG. 4B relates to 48 hours incubation). Similar to Example 3, the results are presented as normalized values relative to "no treatment" results.

As shown in FIG. 4, the fluorescence intensity (MFI) of BFP increased in the presence of erythromycin, either after incubation of 24 hours or 48 hours (FIG. 4A and FIG. 4B, respectively), demonstrating the ability of erythromycin to facilitate read-through of the complete fusion protein comprising GFP and BFP.

In addition to the FACS analysis described above, the transfected cells were lysed and subjected to a Western blot assay using an α-GFP antibody. FIG. 5 presents the results obtained in a Western blot assay performed for cells transfected with plasmids comprising nucleic acid inserts that comprise the nonsense mutations associated with the ATM and the Usher syndrome described above.

As demonstrated in FIG. 5, the "WT" band which corresponds to 55 kilodalton (kDa) represents the full length fusion protein comprising both GFP and BFP flanking a short sequence of the tested protein. Remarkably, as can be seen in FIG. 5, upon erythromycin treatment, a similar sized band also appeared for the mutated sequences ("ATM mut" and "Usher mut").

As clearly shown in FIG. 5, the high-molecular size band corresponding to the full length fusion protein is only a fraction of the total protein (GFP alone), suggesting a modest yield of read-through. These protein expression results confirm that the macrolide erythromycin can read-through nonsense disease-causing mutations.

Example 6

Methyl-CpG Binding Protein-2 (MeCP2) Protein Restoration in Fibroblasts Using Macrolides MeCP2 Protein Expression was evaluated in Rett Syndrome fibroblasts. Rett syndrome fibroblasts (a generous gift from Dr. Ben-Zeev, Sheba hospital) containing the nonsense mutation 880C>T (i.e. R294X) were treated for 7 days with Erythromycin or Azithromycin, in comparison to the well-established aminoglycoside Gentamicin (G418).

As clearly demonstrated in FIG. 6, MeCP2 was expressed only in the presence of the above compounds, at variable levels, in comparison to non-treated cells, where in the presence of Azithromycin slightly more MeCP2 was expressed. As shown in FIG. 6, a dose response analysis of Azithromycin demonstrated high expression even at a low dose of 10 µg/ml. This observation suggests putative low doses to be administered to patients suffering from Rett Syndrome which results from stop codon mutations.

Example 7

MeCP2 Nuclear Localization

After the restoration of MeCP2 protein was demonstrated in the presence of macrolides, the functional activity of the expressed MeCP2 protein was assayed in fibroblasts obtained from Rett syndrome patients.

As demonstrated in FIG. 7A, which shows staining by antibodies directed to MeCP2 (upper panel) and dapi staining of the nucleus (lower panel) in wild type fibroblasts the protein MeCP2 localizes in the nucleus.

Interestingly, as demonstrated in FIG. 7B and in FIG. 7C, following incubation in the presence of macrolides, the protein MeCP2 was re-localized to the cells nuclei (as indicated by the arrows pointing to cell stained by both dapi and antibodies directed to MeCP2), suggesting its functionality as a transcription factor. As can be seen in FIG. 7D, which is a quantification of the percentage of nuclear staining, the effect of Azithromycin was again the highest among the tested compounds, affecting 50-60% of the cells.

Taken together these results show that Erythromycin and Azithromycin enabled read-through translation of the MeCP2 protein, achieving moderately high levels of MeCP2, which is probably functional, since it localizes to the nucleus.

Example 8

Verifying the Restoration of a Functional Protein in the Rett Syndrome Using Additional Models In the Rett syndrome (RTT), mutations in the methyl-CpG binding protein 2 (MECP2) gene are responsible for the majority of the cases, where different mutations are known, including: Y141, R168, Q170, R198, R255, R256, R270 and R294.

In order to assay the effect of an agent in reading-through a stop codon associated with RTT, the following in vitro experiments are used:

1. Western blot analysis of fibroblasts taken from RTT patients harboring at least one of the above mutations, e.g. as exemplified for R294X above. The analysis compares untreated fibroblasts to fibroblasts treated with a macrolide using nuclear extracts. Western blot assays are also done on a lymphocyte cell line derived from a Rett girl expressing an R255X nonsense mutation of MECP2 (Coriell Cell Repository stock No. 16497)

2. MECP2 RNA levels is determined and compared between untreated and treated RTT fibroblasts.

3. Expression of the MECP2 target gene, namely brain derived neurotrophic factor (BDNF) is measured and compared between untreated and treated RTT fibroblasts.

In addition, the effect of an agent in reading-through a stop codon associated with RTT is also assayed using animal models, for example $Mecp2^{R168X}$ knock-in mice, which is a model for Rett syndrome carrying the R168X mutation in the MECP2 gene, are used. Fibroblasts taken from these mice are examined for the level and subcellular localization of MECP2.

Example 9

Restoring a Full Length SMN2 Protein Using Macrolides

As detailed above, spinal muscular atrophy (SMA) is a genetic disease caused by mutations in the SMN1 (survival motor neuron 1) gene. SMN2 is a nearly identical copy of SMN1, differentiated only by a silent, single-nucleotide transition within exon 7 that disrupts an exonic splicing enhancer. Most of the SMN2 protein product, namely Δ7-SMN is dysfunctional and unstable and the small amount of the functional protein that is produced from SMN2 gene is not able to fully compensate for the loss of SMN1 in SMA patients.

The ability of macrolide to induce expression of full length SMN2 (FL-SMN2) was assayed in Spinal Muscular Atrophy fibroblasts, as detailed below. In order to examine the read-through potential, SMN1 deficient fibroblasts (containing either one (+/−) or two (+/+) copies of the SMN2 gene) were treated for 7 days with Erythromycin or Azithromycin. Cells were also treated with the aminoglycoside Gentamycin, as a positive control.

As clearly demonstrated in FIG. 8A, in the presence of all of the assayed compounds, namely Erythromycin, Azithromycin and the positive control Gentamycin, full-length SMN2 protein (32 kDa, FL-SMN2) was expressed in both types of fibroblasts.

Markedly, the expression of full-length SMN2 was reduced when one allele of the SMN2 gene was also mutated (SMN2+/−) as observed in FIG. 8A compared to FIG. 8B, which show results of corresponding experiments conducted with (SMN2+/+) fibroblasts.

Azithromycin demonstrated slightly higher FL-SMN2 levels in fibroblast from both origins (i.e. SMN1−/−; SMN2+/− and SMN1−/−; SMN2+/+). Furthermore, dose response analysis revealed reversed correlation, demonstrating increasing read-through at decreasing doses, with the highest expression obtained at a low dose of 10 μg/ml Azithromycin. This observation suggests putative low doses for patients' administration.

It is noteworthy that incubation of the fibroblast cells in the presence of Gentamycin or Erythromycin had no effect on the expression of non-related proteins, as demonstrated in FIGS. 8C and 8D, even when the above compounds were used at a high dose of 500 μg/ml.

In addition, treatment using the above compounds was not harmful as the survival rate of the cells remained approximately 90% under the assay conditions, as demonstrated in FIG. 8E.

Thus the above results demonstrate that Erythromycin and Azithromycin allowed read-through translation of the FL-SMN protein.

Example 10

Restoring SMN Activity Using Macrolides in an Animal Model

Following the observation that translation of full-length SM2 may be induced patients' fibroblasts using macrolides, the ability of the macrolide Azithromycin to induce translation of full-length SM2 is also assayed in mice, as described below.

Mice deficient of endogenous Smn1 are non-viable. In an effort to circumvent this embryonic lethality and generate an animal with intermediate SMA phenotype, a human SMN2 transgene was added onto the $Smn1^{-/-}$ background ($Smn1^{-/-}$; $SMN2^{+/+}$), resulting in an animal that surrenders to disease in the first postnatal week. The further addition of a human SMN2 transgene lacking exon 7 onto this model ($Smn1^{-/-}$; $SMN2^{+/+}$; $SMN2\Delta7^{+/+}$) resulted in an animal with a mean lifespan of ~14 days that exhibits progressive muscle weakness associated with neuromuscular junction (NMJ) denervation, as detailed above.

As a first step, the pharmacodynamics of Azythromycin are evaluated. Azythromycin is directly administered into the CNS of SMA mice at low and high doses (as detailed below) in order to perform a toxicity study. The study includes 3 mice groups (vehicle, low and high Azythromycin doses) administered at post-natal day (PND) 3 or 5. Each group contains 25-30 animals, divided by two. Then, since Azythromycin is effective at 10 μg/ml and the volume of the Cerebrospinal fluid (CSF) in a mouse is approximately 35 μl, 1 and 10 μg/mouse will be administered, as the low and high dose, respectively.

As a second step, the pharmacodynamics of Azythromycin are evaluated by monitoring the following parameters: mice survival, muscles capabilities including righting reflex, tube test score, geotaxis, etc and the study endpoints include termination at two time points: half-group at PND 9, during a mid-point of aspired life-span, and the other at PND 14, when mice are at/near their functional death endpoint.

Additional parameters measured are Azythromycin and SMN2 contents in harvested tissues, including brain, kidney, spinal cord and skeletal muscle. Histology of the relevant tissues is also performed.

Example 11

Restoring SMN Activity Using Macrolides in Combination with Other Compounds

As demonstrated above, Azithromycin is active at the translational level of SMN2 expression, namely, Azithromycin is able to induce expression of the SMN protein from the SMN2 gene by read-through translation of SMN2 messenger RNA harboring a stop codon. Two other levels, being transcriptional and post-transcriptional, are targets for treatment with a combination of Azithromycin and an additional compound, as detailed herein below.

Specifically, the following agents are selected for use in clinical studies in combination with macrolides:

(1) Agents that are able to induce transcription—although SMN2 pre-mRNAs are preferentially producing SMNΔ7, a global increase in transcription would increase the full-length as well as the SMNΔ7 mRNA, resulting in a higher level of full length SMN2 (SMN2-FL).

For example, Histone deacetylase inhibitors (HDACi) promote SMN2 transcription enhancement by repressing DNA chromatin compression. Promoter enhancement by the quinazoline derivative, RG3039, which is a scavenger mRNA-decapping enzyme (DcpS, an enzyme involved in 5' cap-mediated degradation of mRNAs) inhibitor (Repligen/Pfizer). It was reported that oral administration of RG3039 resulted in a dose-dependent increase of SMN in SMA mice and extended survival by ~20-30% (19). The quinazoline derivative, RG3039 is therefore used in combination with Azithromycin, in order to increase the SMN2-FL levels.

(2) Agents that are able to induce post-transcriptional modification (Splicing)~namely increasing the SMN-FL/SMNΔ7 ratio from SMN2 by suppressing the alternative splicing event that excises SMN exon 7 from the majority of SMN2-derived transcripts.

To that end the antisense ASO-10-27 molecule is used (ISIS/Biogen/Genzyme). The antisense ASO-10-27 was reported to correct ear and tail necrosis in a mild mouse model of SMA and extend median survival in severe SMA mice from 16 to 26 days after ICV injection (20).

Example 12

Restoration of a Functional Protein in Usher Syndrome (USH)

Approximately 12% of all USH cases result by nonsense mutations. An exemplary nonsense mutation is R31X in the USH1C gene, which encodes the scaffold protein harmonin.

The ability of antibiotic macrolides to induce read-through of nonsense mutations associated with USH is assayed by the following experiments:
1. Immunofluorescence and Western blot analysis of HEK293T cells that are transfected with wild-type or R31X mutant harmonin. Cells transfected with the R31X mutant are treated with a macrolide. Overexpression of harmonin is measured and compared between WT-expressing cells, and R31X mutant-expressing cells with and without the macrolide treatment.
2. Glutathione S-transferase (GST)-pull down assay. In order to test protein function of recovered harmonin, the specific interaction between the harmonin PDZ1 domain and the PBM (PDZ-binding motif) in the cytoplasmic tail of the USH2a isoform b7 is measured.
3. Actin filament bundling. The ability of harmonin to induce actin filament bundling is tested.
4. Retinal assays, explants. A construct containing the mutated harmonin fused to a red-fluorescent protein (RFP) is introduced by electroporation into retina explants of mice. Treatment with a macrolide is applied, and analysis of the RFP expression is performed by fluorescence microscopy.

Example 13

Restoration of a Functional Alpha-1-Iduronidase Gene Product Associated with Hurler Syndrome The two most frequent mutations found in patients with Hurler syndrome, the Q70X and W402X nonsense mutations in the alpha-1-iduronidase (IDUA) gene, are present in ~70% of patients of European descent.

The ability of antibiotic macrolides to induce read-through of nonsense mutations associated with the Hurler syndrome is assayed by the following experiments:
1. Expression of WT and mutated cDNAs of alpha-1-iduronidase in reticulocytes, testing for read-through under treatment. Using a rabbit reticulocyte lysate coupled transcription/translation system (Promega).
2. Obtaining primary human skin fibroblast cell from healthy subjects and patients with IDUA gene mutations. The fibroblast cells are used in the following assays.
3. Immunoquantification assays and Western blot analysis, using specific antibodies.
4. Measuring α-L-iduronidase activity using a fluorogenic substrate, 4-methylumbelliferyl-α-L-iduronide (Glycosynth, Cheshire, UK); 4-methyl-umbelliferone iduronide (FMU) (Calbiochem OR Gold Biotech). The fluorescence of the cleaved free FMU molecule is measured.
5. Measuring glycos-aminoglycan (GAG) accumulation (activity) by radioactive labeling of macromolecules, or using sulfated GAG quantitation with a Blyscan kit (Biocolor Ltd. UK).
6. Detecting normal lysosomal abundance by staining of cells using LysoTracker Red (molecular probes).
7. Tissue cultures assays using mouse embryonic fibroblasts (MEFs) derived from homozygous Idua-W392X and WT mice.
8. CHO-K1 (Q70, W402): CHO-K1 cells expressing a mutated IDUA gene contain no α-L-iduronidase activity detectable by an immune capture assay, which specifically detects human α-L-iduronidase. In contrast. CHO-K1 expression of the full-length wild-type IDUA was found to produce over 30 nmol/min per mg of α-L-iduronidase activity in a cloned cell line.

The ability of antibiotic macrolides to induce readthrough of nonsense mutations associated with the Hurler syndrome is also assayed using an animal model as described below.

A knock-in mouse model of MPS 1-H that carries the Idua-W392X mutation is used, Mice homozygous for this mutant allele, which corresponds to the IDUA-14/402X mutation frequently found in MPS 1-H patients, were found to exhibit a phenotype that closely resembles the human MPS I-H disease. Tissue and urine GAG levels are measured.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method of inducing read-through of a nonsense mutation associated with a genetic neurodegenerative or neurodevelopmental disease in a patient in need thereof, the method comprising i) administering to the central nervous system of said patient a composition comprising a macrolide selected from erythromycin and azithromycin as the sole translational read-through agent in the composition, and ii) detecting an increased expression level of a gene with the nonsense mutation in the patient when compared to the patient with no treatment; wherein the nonsense mutation associated with a genetic neurodegenerative or neurodevelopmental disease is selected from the group consisting of: C5515T or C103T in the gene encoding Ataxia Telangiectasia Mutated (ATM) protein, associated with ataxia telangiectasia; C880T in the gene encoding Methyl-CpG Binding Protein-2(MeCP2), associated with Rett syndrome; and a premature termination codon in the alternatively spliced transcript SMN2Δ7 resulting from C840T in exon 7 of the gene encoding Survival Motor Neuron protein 2 (SMN2), associated with spinal muscular atrophy; and wherein detecting the increased expression level of the gene with the nonsense mutation in the patient is selected from the group consisting of ATM protein in the patient with ataxia telangiectasia; MeCP2 protein in the patient with Rett syndrome; and SMN2 protein in the patient with spinal muscular atrophy.

2. The method of claim 1, wherein said composition is administered via a route of administration selected from the group consisting of intrathecal, intraneural, intra-cerebral, intra-ventricular, and intra-cranial administration.

3. The method of claim 1, wherein said composition is administered intrathecally.

* * * * *

```
                       SEQUENCE LISTING

<160> NUMBER OF SEQ ID NOS: 11

<210> SEQ ID NO 1
<211> LENGTH: 29
<212> TYPE: DNA
<213> ORGANISM: Artificial Sequence
<220> FEATURE:
<223> OTHER INFORMATION: KpnI forward primer

<400> SEQUENCE: 1
agaggtaccg agtgagcaag ggcgaggag                                       29

<210> SEQ ID NO 2
<211> LENGTH: 30
<212> TYPE: DNA
<213> ORGANISM: Artificial Sequence
<220> FEATURE:
<223> OTHER INFORMATION: BamHI reverse primer

<400> SEQUENCE: 2
agaggatccg atccggtgga tcccgggccc                                      30

<210> SEQ ID NO 3
<211> LENGTH: 42
<212> TYPE: DNA
<213> ORGANISM: Homo sapiens

<400> SEQUENCE: 3
aaatttaagc gcctgatttg agatcctgaa acaattaaac at                        42

<210> SEQ ID NO 4
<211> LENGTH: 42
<212> TYPE: DNA
<213> ORGANISM: Homo sapiens

<400> SEQUENCE: 4
aaatttaagc gcctgattcg agatcctgaa acaattaaac at                        42

<210> SEQ ID NO 5
<211> LENGTH: 42
<212> TYPE: DNA
<213> ORGANISM: Homo sapiens

<400> SEQUENCE: 5
tatctctatg atgtgctgcg aatgtaccac cagaccatgg ac                        42

<210> SEQ ID NO 6
<211> LENGTH: 42
<212> TYPE: DNA
<213> ORGANISM: Homo sapiens
```

```
<400> SEQUENCE: 6
tatctctatg atgtgctgtg aatgtaccac cagaccatgg ac                          42

<210> SEQ ID NO 7
<211> LENGTH: 42
<212> TYPE: DNA
<213> ORGANISM: Homo sapiens

<400> SEQUENCE: 7
agagggagcc cctcccggcg agagcagaaa ccacctaaga ag                          42

<210> SEQ ID NO 8
<211> LENGTH: 42
<212> TYPE: DNA
<213> ORGANISM: Homo sapiens

<400> SEQUENCE: 8
agagggagcc cctcccggtg agagcagaaa ccacctaaga ag                          42

<210> SEQ ID NO 9
<211> LENGTH: 717
<212> TYPE: DNA
<213> ORGANISM: Artificial Sequence
<220> FEATURE:
<223> OTHER INFORMATION: green fluorescence protein

<400> SEQUENCE: 9
atggtgagca agggcgagga gctgttcacc ggggtggtgc ccatcctggt cgagctggac        60
ggcgacgtaa acggccacaa gttcagcgtg tccggcgagg gcgagggcga tgccacctac       120
ggcaagctga ccctgaagtt catctgcacc accggcaagc tgcccgtgcc ctggcccacc       180
ctcgtgacca ccctgaccta cggcgtgcag tgcttcagcc gctaccccga ccacatgaag       240
cagcacgact tcttcaagtc cgccatgccc gaaggctacg tccaggagcg caccatcttc       300
ttcaaggacg acggcaacta caagacccgc gccgaggtga agttcgaggg cgacaccctg       360
gtgaaccgca tcgagctgaa gggcatcgac ttcaaggagg acggcaacat cctggggcac       420
aagctggagt acaactacaa cagccacaac gtctatatca tggccgacaa gcagaagaac       480
ggcatcaagg tgaacttcaa gatccgccac aacatcgagg acggcagcgt gcagctcgcc       540
gaccactacc agcagaacac ccccatcggc gacggccccg tgctgctgcc cgacaaccac       600
tacctgagca cccagtccgc cctgagcaaa gaccccaacg agaagcgcga tcacatggtc       660
ctgctggagt tcgtgaccgc cgccgggatc actctcggca tggacgagct gtacaag         717

<210> SEQ ID NO 10
<211> LENGTH: 720
<212> TYPE: DNA
<213> ORGANISM: Artificial Sequence
<220> FEATURE:
<223> OTHER INFORMATION: blue fluorescent protein

<400> SEQUENCE: 10
atggtgagca agggcgagga gctgttcacc ggggtggtgc ccatcctggt cgagctggac        60
ggcgacgtaa acggccacaa gttcagcgtg tccggcgagg gcgagggcga tgccacctac       120
ggcaagctga ccctgaagtt catctgcacc accggcaagc tgcccgtgcc ctggcccacc       180
ctcgtgacca ccctgagcca cggcgtccag tgcttcagcc gctaccccga ccacatgaag       240
cagcacgact tcttcaagtc cgccatgccc gaaggctacg tccaggagcg caccatcttc       300
ttcaaggacg acggcaacta caagacccgc gccgaggtga agttcgaggg cgacaccctg       360
```

```
gtgaaccgca tcgagctgaa gggcatcgac ttcaaggagg acggcaacat cctgggcac    420 aagctggagt acaacttcaa cagccacaac gtctatatca tggccgacaa gcagaagaac    480
ggcatcaagg cgaacttcaa gatccgccac aacatcgagg acggcagcgt gcagctcgcc    540
gaccactacc agcagaacac ccccatcggc gacggccccg tgctgctgcc cgacagccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtaa    720

<210> SEQ ID NO 11
<211> LENGTH: 1536
<212> TYPE: DNA
<213> ORGANISM: Homo sapiens

<400> SEQUENCE: 11
agaagccccg gcggcggaa gtcgtcactc ttaagaaggg acggggcccc acgctgcgca     60
cccgcgggtt tgctatggcg atgagcagcg gcggcagtgg tggcggcgtc ccggagcagg    120
aggattccgt gctgttccgg cgcggcacag gccagagcga tgattctgac atttgggatg    180
atacagcact gataaaagca tatgataaag ctgtggcttc atttaagcat gctctaaaga    240
atggtgacat ttgtgaaact tcgggtaaac caaaaaccac acctaaaaga aaacctgcta    300
agaagaataa aagccaaaag aagaatactg cagcttcctt acaacagtgg aaagttgggg    360
acaaatgttc tgccatttgg tcagaagacg gttgcattta cccagctacc attgcttcaa    420
ttgattttaa gagagaaacc tgtgttgtgg tttacactgg atatgaaat agagaggagc    480 aaaatctgtc cgatctactt tccccaatct gtgaagtagc taataatata gaacaaaatg    540
ctcaagagaa tgaaaatgaa agccaagttt caacagatga aagtgagaac tccaggtctc    600
ctggaaataa atcagataac atcaagccca aatctgctcc atggaactct tttctccctc    660
caccaccccc catgccaggg ccaagactgg gaccaggaaa gccaggtcta aaattcaatg    720
gcccaccacc gccaccgcca ccaccaccac cccacttact atcatgctgg ctgcctccat    780
ttccttctgg accaccaata attccccac cacctcccat atgtccagat tctcttgatg    840
atgctgatgc tttgggaagt atgttaattt catggtacat gagtggctat catactggct    900
attatatggg ttttagacaa aatcaaaaag aaggaaggtg ctcacattcc ttaaattaag    960
gagaaatgct ggcatagagc agcactaaat gacaccacta agaaacgat cagacagatc    1020 tggaatgtga agcgttatag aagataactg gcctcatttc ttcaaaatat caagtgttgg    1080
gaaagaaaaa aggaagtgga atgggtaact cttcttgatt aaaagttatg taataaccaa    1140
atgcaatgtg aaatatttta ctggactcta ttttgaaaaa ccatctgtaa aagactgagg    1200
tgggggtggg aggccagcac ggtggtgagg cagttgagaa aatttgaatg tggattagat    1260
tttgaatgat attggataat tattggtaat tttatgagct gtgagaaggg tgttgtagtt    1320
tataaaagac tgtcttaatt tgcatactta agcatttagg aatgaagtgt tagagtgtct    1380
taaaatgttt caaatggttt aacaaaatgt atgtgaggcg tatgtggcaa aatgttacag    1440
aatctaactg gtggacatgg ctgttcattg tactgttttt ttctatcttc tatatgttta    1500
aaagtatata ataaaaatat ttaatttttt tttaaa                              1536
```